United States Patent
Butte et al.

(10) Patent No.: US 10,426,403 B2
(45) Date of Patent: Oct. 1, 2019

(54) METHODS OF TESTING FOR ALLERGEN SENSITIVITY

(71) Applicant: The Board of Trustees of the Leland Stanford Junior University, Stanford, CA (US)

(72) Inventors: Manish J. Butte, Stanford, CA (US); Jayakumar Rajadas, Cupertino, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 294 days.

(21) Appl. No.: 14/888,689

(22) PCT Filed: May 8, 2014

(86) PCT No.: PCT/US2014/037347
§ 371 (c)(1),
(2) Date: Nov. 2, 2015

(87) PCT Pub. No.: WO2014/182932
PCT Pub. Date: Nov. 13, 2014

(65) Prior Publication Data
US 2016/0058377 A1    Mar. 3, 2016

Related U.S. Application Data

(60) Provisional application No. 61/821,112, filed on May 8, 2013, provisional application No. 61/988,082, filed on May 2, 2014.

(51) Int. Cl.
*A61B 5/00* (2006.01)
*A61M 37/00* (2006.01)
*A61B 5/01* (2006.01)

(52) U.S. Cl.
CPC ............ *A61B 5/685* (2013.01); *A61B 5/0077* (2013.01); *A61B 5/015* (2013.01); *A61B 5/411* (2013.01);
(Continued)

(58) Field of Classification Search
CPC ....... A61B 5/0077; A61B 5/015; A61B 5/411; A61B 5/6832; A61B 5/685;
(Continued)

(56) References Cited

U.S. PATENT DOCUMENTS

2005/0181521 A1 *   8/2005   Niskanen ............. G01N 33/558
                                                                436/514
2010/0030100 A1    2/2010   Tokumoto et al.
(Continued)

FOREIGN PATENT DOCUMENTS

| WO | 2007/064486 | 6/2007 |
|----|-------------|--------|
| WO | 2009/008951 | 1/2009 |
| WO | 2012/154284 | 11/2012 |

OTHER PUBLICATIONS

Sun et al. 'Polyvinylpyrrolidone microneedles enable delivery of intact proteins for diagnostic and therapeutic applications,' Acta Biomaterialia, May 3, 2013 (May 3, 2013), vol. 9, pp. 7767-7774.*

*Primary Examiner* — Mark D Remaly
(74) *Attorney, Agent, or Firm* — Pamela J. Sherwood; Bozicevic, Field & Francis LLP

(57) ABSTRACT

A method of testing for specificity and strength of an allergic reaction is performed by penetrating the skin of an individual with the microneedle array comprising a plurality of epitopes and determining the response of the skin to the allergens. The response can be measured with a thermal imaging device. Analysis, and optionally treatment, can be provided to the individual.

21 Claims, 11 Drawing Sheets

(52) U.S. Cl.
CPC . *A61M 37/0015* (2013.01); *A61M 2037/0046* (2013.01); *A61M 2037/0053* (2013.01); *A61M 2037/0061* (2013.01)

(58) Field of Classification Search
CPC .. A61M 2037/0046; A61M 2037/0053; A61M 2037/0061; A61M 37/0015
See application file for complete search history.

(56) References Cited

U.S. PATENT DOCUMENTS

2011/0270122 A1   11/2011   Mir et al.
2014/0080730 A1*   3/2014   Dreskin ............. G01N 33/6854
                                                         506/9

* cited by examiner

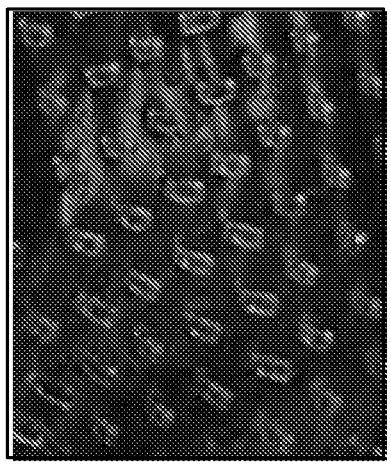
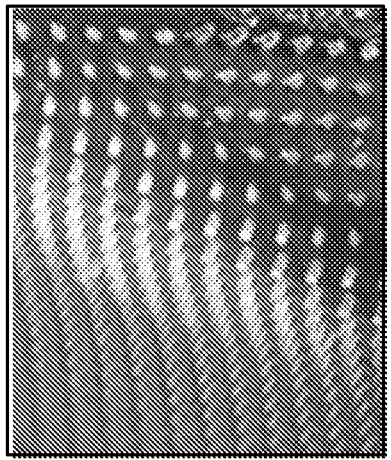
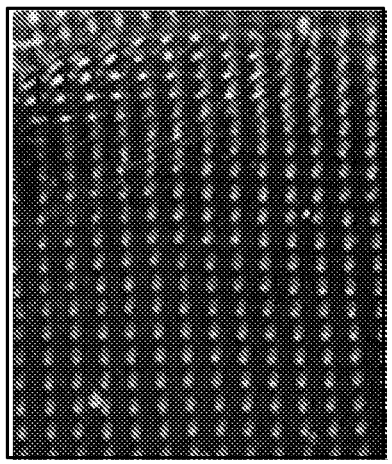
Fig. 1A
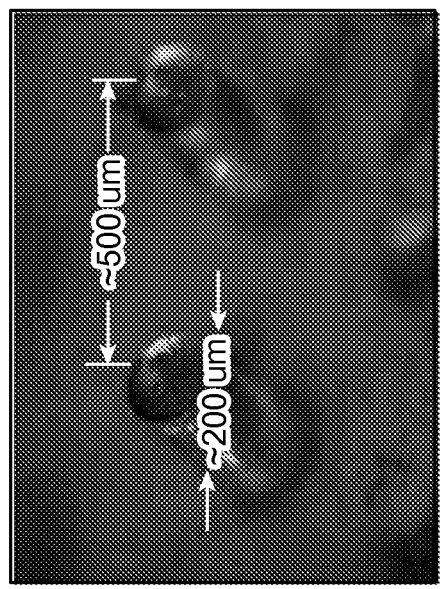
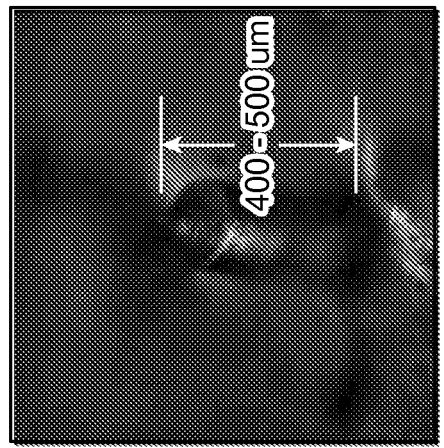
Fig. 1B

PVP-Casein microneedle  PVP-Peanut microneedle  PVP microneedle ctrl

Fig. 4A
Fig. 4B
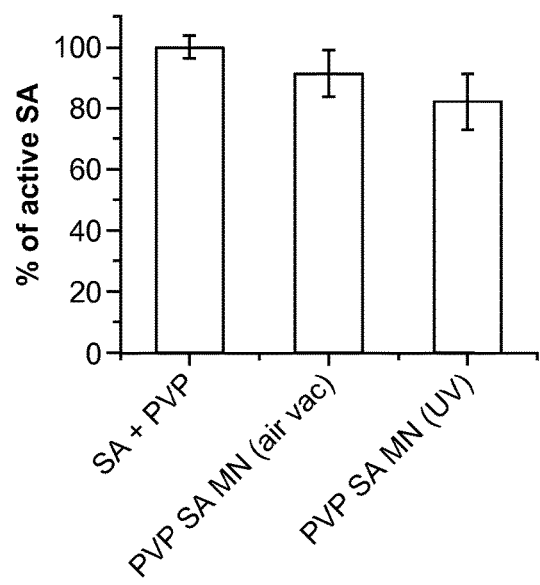
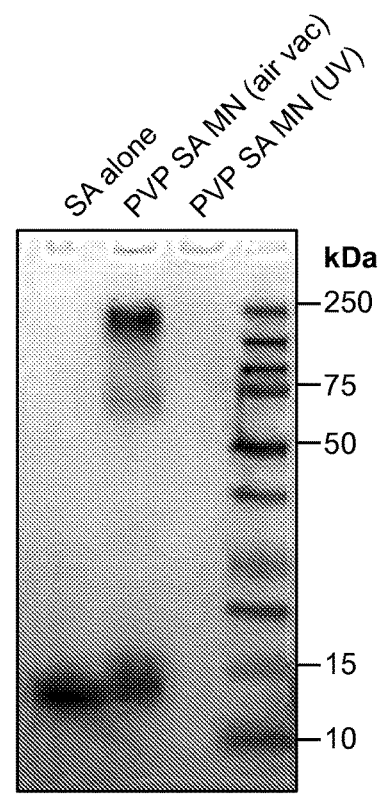

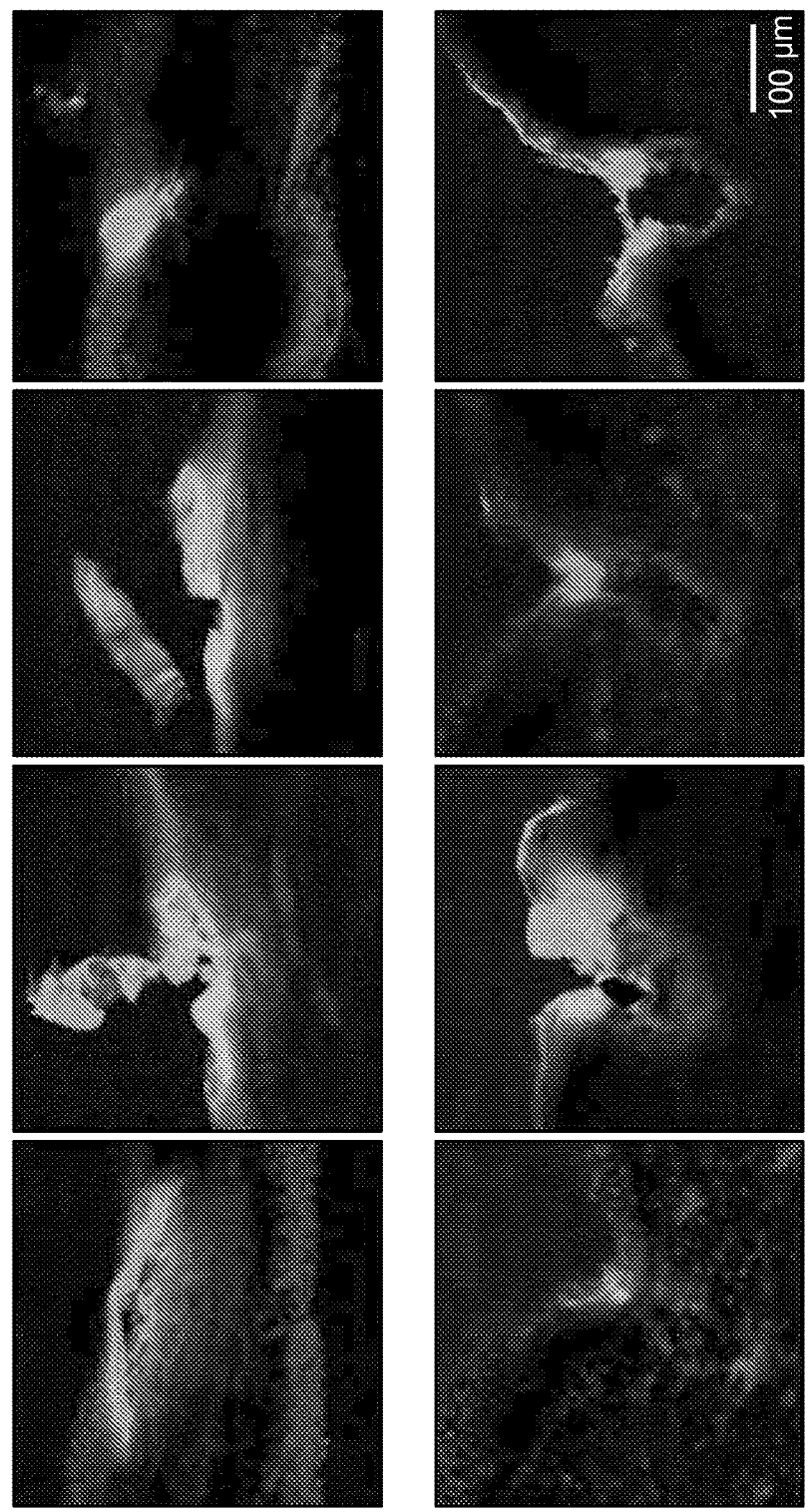

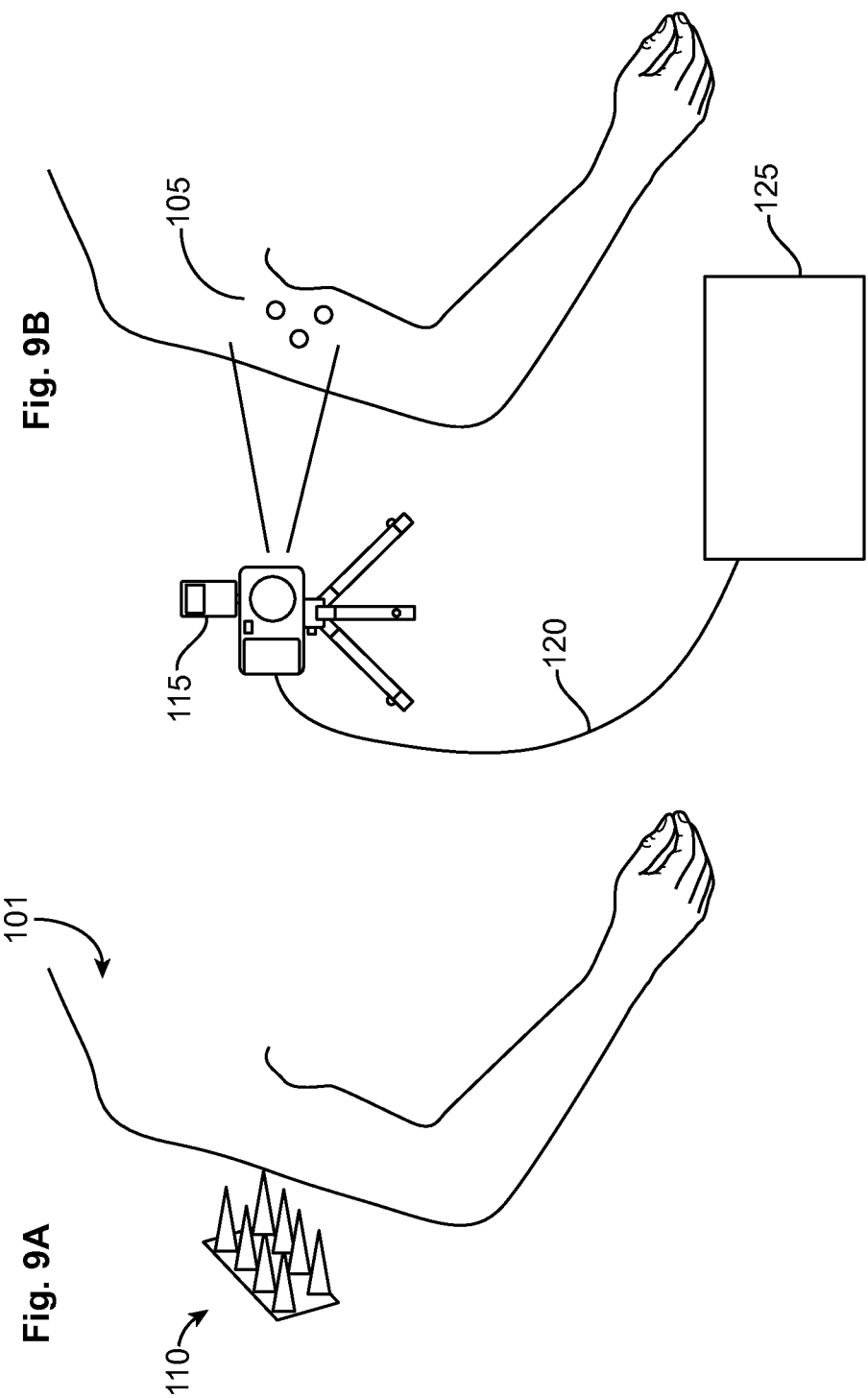

METHODS OF TESTING FOR ALLERGEN SENSITIVITY

FEDERALLY SPONSORED RESEARCH AND DEVELOPMENT

This invention was made with Government support under contract AR047223 awarded by the National Institutes of Health. The Government has certain rights in the invention.

INTRODUCTION

Human skin is equipped with networks of antigen presenting cells that are first to react in the innate immune response. Delivering antigens and adjuvants to these cells in the skin can trigger innate and adaptive immune responses for both diagnostic and therapeutic purposes. For example, see Zhu et al. (2009) PNAS 106:7968-73; Choi et al. (2012) Biomaterials 33:3756-69; and Sullivan et al. (2010) Nature Medicine 16:915-20.

Because of defects in peripheral tolerance in allergic patients, contact or ingestion of allergenic proteins can trigger production of specific immunoglobulin E (IgE) antibodies, which are responsible for subsequent allergic reactions through binding and allergen-induced crosslinking of the IgE receptor (FcεRI) on mast cells. The prevalence of allergic diseases has increased in developed countries over the last few decades and these disorders now consume over $7 billion in healthcare expenditures annually in the USA. It is estimated that approximately 8% of children have true food allergies, but over 20% of children make alterations to their diets because of perceived adverse reactions to food. Anaphylaxis due to food allergy results in over 20,000 hospital visits and 100-200 deaths per year.

The gold standard, diagnostic test for food allergy is a double-blind placebo controlled food challenge (DBPCFC), but these challenges are complicated when multiple foods are considered potential allergens, are difficult or impossible in young children, and are potentially dangerous because the readout is an allergic or anaphylactic response. Hence, skin prick testing (SPT) and serum IgE testing have been mainly used as surrogate tests to predict the risk of failure in a DBPCFC. In general, serum IgE testing is quantitative but rife with false positives and negatives, especially in patients with atopic dermatitis who have high baseline IgE levels. On the other hand, qualitative skin testing can be predictive of DBPCFC, because it is a functional test of mast cell responses in the skin due to the allergen. Unfortunately, because of the limitations of existing needles, only thirty or so of the thousands of potential allergenic peptides can be feasibly tested in a day.

Conventional SPT uses an ensemble of proteins (generally, solvent extracted hydrolysates of mechanically crushed foods), which, because of the massive numbers of epitopes probed, shows only the likelihood of allergic response, not the severity. it is of interest that experiments performed with sequential, linear peptides coated on glass slide microarrays showed that the number of epitopes sensed by IgEs is proportional to the severity of reaction. This finding appears to be general, as testing peptides from peanut, milk, egg, salmon, and lentil in microarrays showed similar results. However, this method is not suitable for broad clinical application because of the need for a microarray slide scanner and the high false positives and negatives inherent in blood testing for allergens. See, for example, Shreffler et al. (2004) J Allergy Clin Immunol. 113:776-82; Cerecedo et al. (2008) J Allergy Clin Immunol. 122:589-94; Perez-Gordo et al. (2011) Int Arch Allergy Immunol. 157:31-40; and Shreffler et al. (2005) J Allergy Clin Immunol. 116:893-9.

It has also been shown that individuals with persistent allergy recognize a larger number of sequential epitopes, including some that appear to be specific or "informative" epitopes, as compared to those individuals who outgrow their food allergy. Specific host or stochastic factors may induce certain individuals to generate an immune response that is more broad-based or biased toward recognition of certain determinants. Even among patients with persistent allergy, analysis of the patterns of IgE epitope binding may be informative.

A functional test that measures biological responses to a highly parallel array of allergenic peptides is of great interest for clinical diagnostic and therapeutic methods. Furthermore, immunotherapy directed at the specific epitopes causing allergic responses could be useful for engendering tolerance, but until now, it has not been practical to deliver potentially hundreds or thousands of specific peptides for immunotherapy. The present invention addresses this need.

SUMMARY OF THE INVENTION

Compositions and methods are provided for determining the allergic response of an individual to one or more allergens of interest. The epitope specificity and strength of response may be determined, as well as the identification of specific allergens to which the individual is responsive. In some embodiments, an analysis is provided to the individual following the determination of allergic responses. In some embodiments, the individual is treated in accordance with the findings, e.g. by counseling on diet and lifestyle, sensitization treatment, provision of suitable anaphylactic measures such as epinephrine, and the like.

In the methods of the invention, a microneedle array, including without limitation a dissolving microneedle array as described herein, comprising one or more epitopes of macromolecules, particularly proteins and peptides derived therefrom, is brought into contact with the skin of the individual to be tested and pressed down into the skin, so as to deliver the epitopes to the intradermal space. In preferred embodiments, the microneedles provide a spatial array of a plurality of peptides corresponding to one or more proteins suspected of being an allergen for the individual, where the total number of different proteins may be at least 1, at least 2, at least 3, at least 4, at least 5, at least 6, at least 7, at least 8, at least 9, at least 10, and may be up to 15, up to 20, up to 25 or more. An array may comprise, for each protein that is being tested, up to and including 1, 2, 3, 4, 5, 7, 10, 12, 15, 17, 20, 22, 25, 27, 30, 32, 35, 37, 40, 42, 45, 47, 50 or more different epitopes, where, for example, each epitope may be represented as a peptide of from about 5 to about 15 amino acids in length. Peptides may be contiguous or non-contiguous segments of the protein, and may be overlapping or non-overlapping. Microneedle replicates may be provided for each epitope, and controls may be included, e.g. known allergens, histamine, etc. The total number of epitopes in an array may be up to 10, up to 100, up to 1000, up to $10^4$, or more epitopes in a single array.

The array may be adhered to a backing so as to securely position to the skin. A backing of interest can be a rigid or flexible support. For some embodiments of the invention, the backing is transparent to ultraviolet radiation, e.g. a glass slide or coverslip. Following delivery, the microneedles deliver the protein and/or peptides to the intradermal space, where an immune response will be generated in an allergic individual. In some embodiments of the invention, the backing is removed for an analysis of responsiveness. In other embodiments, the backing is not removed for an analysis of responsiveness.

If the individual being tested has an allergic response to one or more epitopes present on the microarray, the skin will respond rapidly, typically within no more than about 15 minutes, by release of histamine, mast cell degranulation, etc. The response can be detected visually or thermally. In some embodiments, one or more images may be captured at the site where the array has penetrated the skin, e.g. a visual image, for example reddening of the injection site, a thermal image, and the like. Images can be captured at one or more time points following microneedle injection, e.g. within about 10 seconds, within about 30 seconds, within about 60 seconds, within about 2 minutes, 3 minutes, 4 minutes, 5 minutes, and up to 10 minutes, up to 15 minutes, etc.

Each of the captured images can be analyzed to assess the degree of reaction over the array of epitopes, and to generate a report of the information to be provided to the individual. In some embodiments the images are captured with a camera in visible light. In other embodiments, the image capture is performed with a thermal camera, where an increase of heat in the skin is detected at the point where an allergen is present. A camera may be secured to the individual, secured to the backing of the array, aligned with a fixed point of reference, and the like.

An algorithm is optionally applied in the analysis, which algorithm can include the assessment of one or more parameters including, without limitation, the degree of response, e.g. heat or reddening, the speed of response, the number of epitopes that elicit a response, the percent of epitopes in a given protein that elicit a response, the number of related proteins containing epitopes that elicit a response, weighting of a response to epitopes that are associated with more severe or less severe allergies; and the like.

In some embodiments a bioinformatics method is provided for that selection of epitopes, e.g. peptides, with the improved accuracy for classifying clinically relevant allergic responses. An algorithm incorporates an analysis of epitopes relevant to a determination of severity and/or persistence of an allergic reaction. Such an algorithm is useful in determination weighting of epitopes when assessing an individual response. Parameters of interest include one or more of: proportion of epitopes that elicit a positive response; threshold number of epitopes that elicit a positive response; speed of response; kinetics of response; absolute level of thermal or visual response; etc.

In some embodiments an allergy testing system is provided. The allergy testing system includes a microneedle array, e.g. a dissolving microneedle array, wherein an array of epitopes are encapsulated in the spatial array of microneedles, for example providing up to 10, up to 100, up to 1000, up to $10^4$, or more epitopes in a single array. The allergy testing system may further comprise a suitable backing to adhere the microneedle array to the skin. The system may optionally comprise a device for imaging, including a visual or thermal camera, and imaging software for analysis of responsiveness to the epitope array.

In some embodiments a kit is provided for use in the system, where a kit comprises a microneedle array comprising one or a panel of allergens. Sets of allergens may include, without limitation, environmental allergens, e.g. pollens; insect allergens, e.g. bee venom, spider venom, etc.; food allergens, e.g. fish, shellfish (shrimp, crab, lobster, oyster, scallops), soy, strawberries, tree nuts (walnut, hazel/filbert, cashew, pistachio, Brazil, pine nut, almond), peanuts, milk, egg protein, etc.; drug allergens, e.g. penicillin, etc. For example, a panel of insect allergens may comprise epitopes from a plurality of insect venoms, e.g. *Myrmecia pilosula*; *Apis mellifera* bee venom phospholipase A2 ($PLA_2$) and antigen 5S; phospholipases from the yellow jacket *Vespula maculifrons* and white faced hornet *Dolichovespula maculate*, etc. A panel of pollen allergens may comprise epitopes from a plurality of plants, e.g. birch pollen, ragweed pollen, ParoI (the major allergen of *Parietaria officinalis*) and the cross-reactive allergen ParjI (from *Parietaria judaica*), and other atmospheric pollens including *Olea europaea*, *Artemisia* sp., *gramineae*, etc.

Allergens of interest for analysis by the methods of the invention include, without limitation, allergens associated with anaphylaxis, which include food allergens, insect allergens and drug allergens. Allergens known to be associated with anaphylaxis include food allergens: peanuts, tree nuts, fish, shellfish, cow's milk, soy, and eggs; insect allergens, particularly from stinging insects, e.g. honeybees, fire ants, yellow jackets, yellow hornets and paper wasps; drugs: β-lactams; nonsteroidal anti-inflammatory drugs (NSAIDs); biologic modifiers, e.g. cetuximab, infliximab and omalizumab. Suitable panels comprising an epitope array from one or more if these allergens are provided.

Methods are provided for the preparation of arrays of dissolving polyvinylpyrrolidone (PVP) microneedles, which microneedles encapsulate biological macromolecules of interest, including without limitation, allergens. The microneedle arrays are prepared in the absence of photopolymerization, and do not require adherence to a separately manufactured base. In some embodiments of the invention, the biological macromolecule of interest is an antigenic compound, frequently proteins, peptides, polysaccharides, etc. An advantage of the methods of the invention is the ability to effectively deliver intact and biologically active proteins to the intradermal space, including conformational epitopes of antigens of interest. In some embodiments an array of epitopes are encapsulated in a spatial array of microneedles, for example providing up to 10, up to 100, up to 1000, up to $10^4$, or more epitopes in a single array. By integrating allergen peptides and polysaccharides within the microneedles in an array, a library of candidate allergens can be tested in a single assay.

The microneedle arrays of the invention use the self-assembling properties of polyvinylpyrrolidone (PVP) in aqueous and alcoholic solutions to make microneedles. Methods of manufacture comprise dissolving a biological macromolecule of interest in a suitable excipient, and mixing with a solution of PVP, to which polyethylene glycol is added. Optionally saccharides are included for improved strength and stability, e.g. trehalose, sucrose, lactose, maltose, etc. The resulting mixture is cast in a microneedle mold, e.g. a PDMS mold. The mold can comprise a patterned surface that provides for superhydrophobicity, such that a drop of the solution will tend to specifically enter the targeted microneedle mold. After exposure to a vacuum to remove air from needle chambers, the needles are dried. The drying process results in microneedles of consistent shape and spacing that reflects the dimension of the mold. As the polymer solution dries, PVP fibrils are deposited on the periphery of the drying solution, resulting in encapsulation of the intact and biologically active macromolecule in a microneedle that rapidly dissolves upon exposure to a fluid environment, for example following deposition in the skin.

BRIEF DESCRIPTION OF THE DRAWINGS

FIG. 1A-1B. Microscopic images of labeled allergen microneedles. FIG. 1A) Microneedles incorporated with rhodamine-labeled peanut protein (left), FITC-labeled casein protein (middle) and DQ-ovalalbumin (right). FIG. 1B) Dimensions of microneedles are shown, consistent with the PDMS mold.

FIG. 2A) (Row 1) Microneedle array of PVP-casein, PVP-peanut proteins and PVP alone (Control). (Row 2) Magnified single microneedle showing the surface morphology. FIG. 2B) Morphology of the interior of the broken microneedle. FIG. 2C) Schematic representation of aggregate separation and packed arrangement of the PVP fibers.

FIG. 3A) Schematic representation showing the vertical and horizontal cross section of a rhodamine B labeled casein microneedle. FIG. 3B) Vertical optical cross section. FIG. 3C) Transverse optical cross section. FIG. 3D) Rendered view of 3D reconstructed microneedle. The protein is concentrated in concentric layers beneath the surface.

FIG. 4A-4B. Characterization of streptavidin (SA) recovered from microneedles. FIG. 4A) SA recovered from PVP-SA microneedles retained its biotin binding activity. The intactness of SA was evaluated by measuring the amount of unbound biotin using a biotin quantitation assay (n=3, mean±SD). FIG. 4B) SDS-PAGE of SA recovered from microneedles. Lane 1: control SA; Lane 2: PVP-SA microneedles prepared using air-vacuum method; Lane 3: PVP-SA microneedles prepared using UV-photo crosslinking method.

FIG. 5A) Schematic representation showing the experimental setup. FIG. 5B) Microneedles dissolve in human foreskin. Images are microneedles prior to insertion or remaining on the Tegaderm 1, 2.5 and 5 min after insertion into human foreskin.

FIG. 6A-6B. Penetration of microneedles into skin. Fluorescent images showing comparison of penetration of PVP-rhodamine B labeled casein microneedles and casein coated AdminPatch array 1200 steel needles into human foreskin. Blue, DAPI staining; Red, rhodamine B. Four representative penetration sites are shown for each type of microneedle.

FIG. 7A) PDMS mold with six patches used to prepare the array. FIG. 7B) An array of six PVP microneedles labeled with alternating fluorescent dyes (fluorescein and rhodamine B) peeled off the mold by a Tegaderm patch. FIG. 7C) Images of individual microneedle patches in the array. FIG. 7D) Image of the microneedles array under UV illumination.

FIG. 9A-9B. A schematic of allergen testing.

DESCRIPTION OF THE SPECIFIC EMBODIMENTS

Figure 2A:
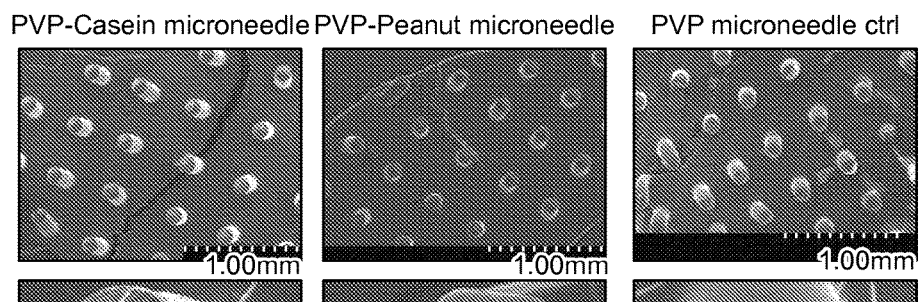
FIG. 2A-2C. Scanning electron microscopy images of microneedles.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

Methods and compositions for determining the presence and specificity of an allergic response of an individual are provided. In certain aspects, these methods and compositions can be useful to substitute for, or complement existing skin-prick tests for determining allergies. In the methods of the invention, an array of microneedles comprising a plurality of epitopes are contacted and penetrated into the skin of the individual. Contact with the allergen in a responsive individual results in mast cell degranulation and release of histamines, heparin, eosinophil and neutrophil chemotactic factors, leukotrienes and thromboxanes, etc. A hypersensitive response will cause rapid production of heat, and a visible wheal and erythema within about 15 minutes. The pattern of response, e.g. intensity of response, rapidity and kinetics of response, on the skin is indicative of the specificity and intensity of the response. In addition, the number of different epitopes from an allergen of interest to which the individual reacts is indicative of the severity to which the individual will react to that allergen. In some embodiments, the allergen is a protein, and epitopes are provided as peptides of that protein, for example a series of overlapping or non-overlapping peptide fragments of the allergen. In other embodiments the allergen is one or more polysaccharides.

The terms "individual" and "subject" are used interchangeably to refer to any mammal including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs. Pediatric testing is particularly relevant in human populations, including pediatric populations.

An "immunological response" or "immune response" against a selected agent or a composition of interest is the development in an individual of a humoral and/or a cellular immune response to molecules present in the agent or composition of interest. Of particular interest is an immediate hypersensitivity mediated through the interaction of IgE molecules bound to mast cell and other mediators.

Microneedle Array. The use of microneedles in transdermal and intradermal delivery is advantageous as intracutaneous drug delivery or drug sampling can be accomplished by penetrating the outer layer of the skin without pain and bleeding. As used herein, the term "microneedles" refers to a plurality of elongated structures that are sufficiently long to penetrate through the stratum corneum skin layer into the epidermal or dermal or subcutaneous layer. In general, the microneedles are not so long as to penetrate into the dermal layer.

A microneedle array comprises a plurality of microprojections, generally ranging from at least about 25 µm in length, at least about 100 µm in length, at least about 250 µm in length, at least about 500 µm in length, and not more than about 2000 µm in length, usually not more than about 1000 µm in length. In some embodiments the range is from about 100 to about 1000 µm in length; and some embodiments from about 250 to 750 µm in length. The microneedles are attached to a base support, which is conveniently cast with the microneedles, i.e. a separate attachment step to the base is not required. An array may comprise $10^2$, $10^3$, $10^4$, $10^5$ or more microneedles, and may range in area from about 0.1 $cm^2$ to about 100 $cm^2$. In some embodiments of the invention, the microneedle array is formulated as a transdermal delivery patch, i.e. where the array is adhered to a patch of adhesive material that allows it to be fixed to the skin. Application of MN arrays to biological membranes creates transport pathways of micron dimensions, which readily permit transport of macromolecules such as peptides and proteins.

The distance between needles on an array will vary, depending on the size of the plate and the number of needles present. Typically, needles will be placed at a distance from 5 µm to 5000 µm from each other, such as from 100 to 3000 µm apart, 250 to 1000 µm apart, or any distance within these ranges. The plate can include any number of microneedles, such as 1 to 1,000,000, typically, 10 to 100,000, such as 50 to 10,000, 100 to 1000, or any number within these ranges.

Figure 10C:
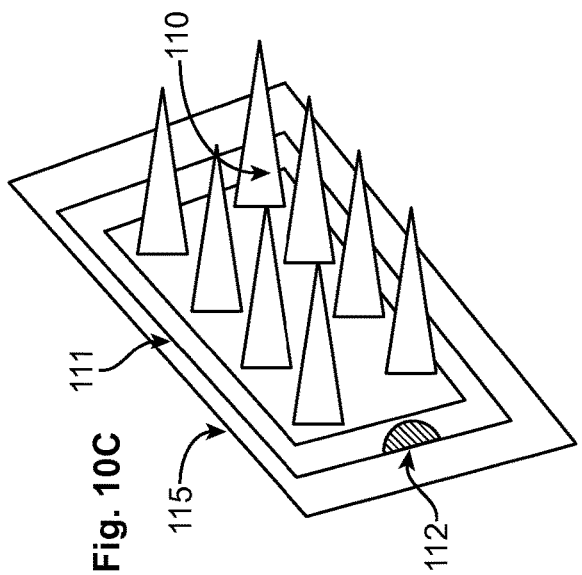
FIG. 10A-10C. A schematic showing backings of the microneedle array.
Figure 10A:
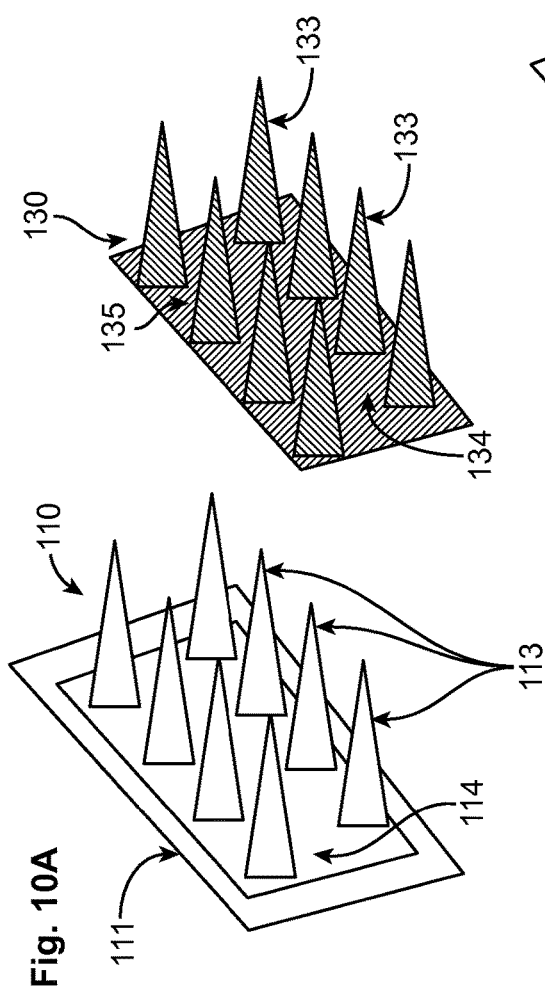
Figure 10B:
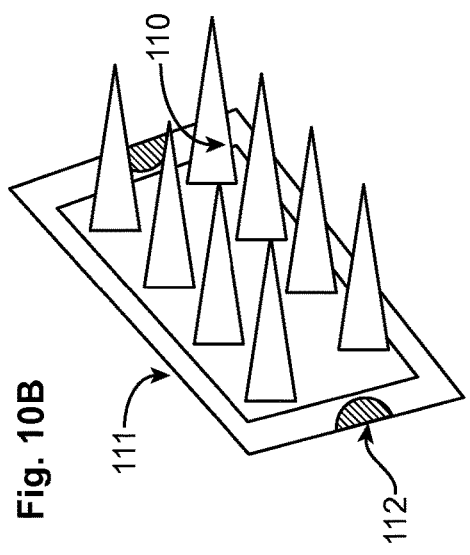
Figure 11:
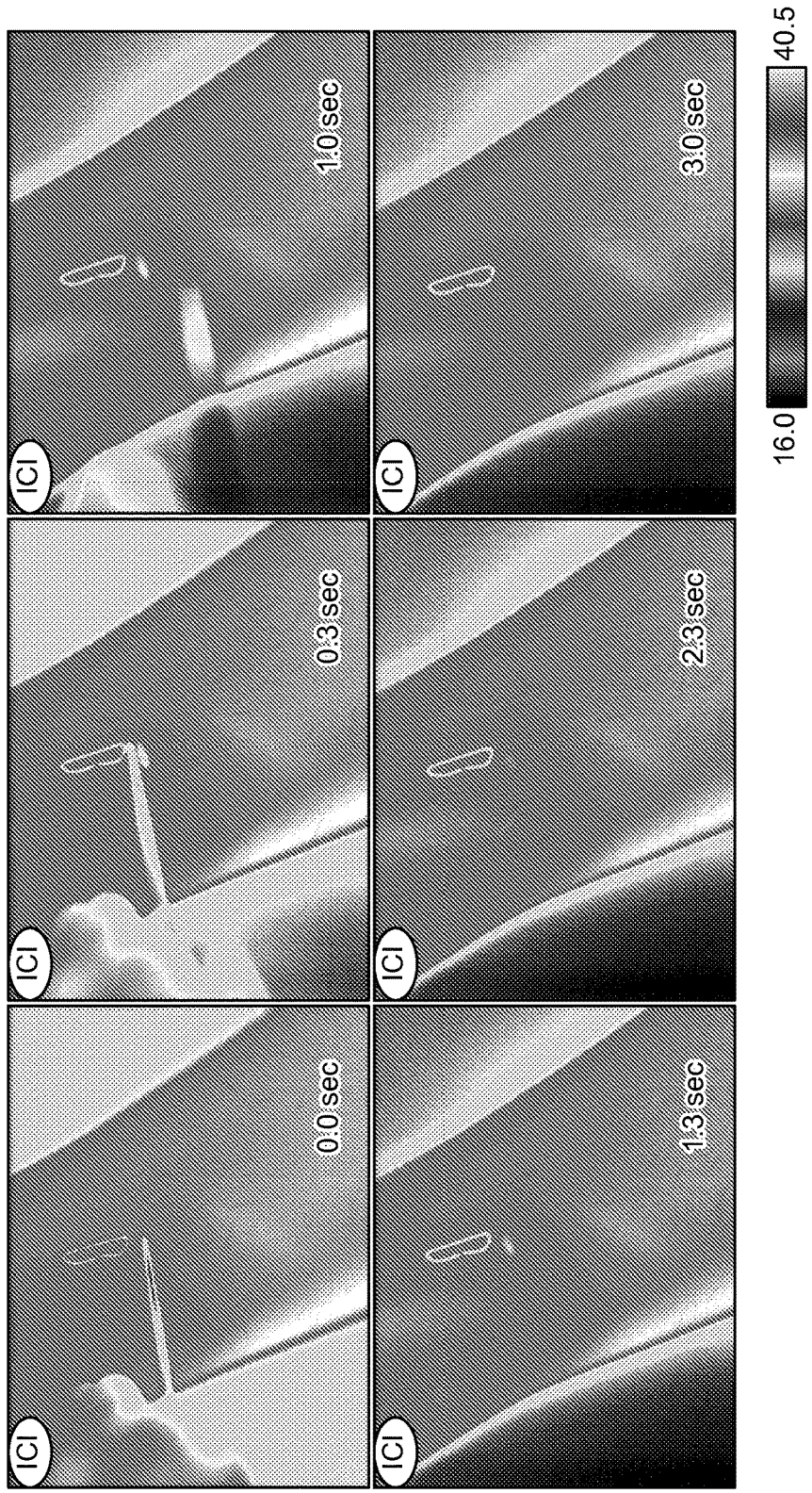
FIG. 11. Thermal imaging of skin. Thermal image of a forearm placed under the camera at a distance of five inches with a staple placed on the skin as landmark to pinpoint the location. A needle was chilled on ice for five minutes then placed onto the skin for one second. Skin temperature at the point of contact is 27.5° C. when it was removed. Skin temperature quickly increased back to skin temperature in three seconds at 30.8° C. These sequential images demonstrate the use and accuracy of a thermal camera to detect minute changes in the skin temperature.

As shown in FIGS. 10A-10C, the microneedle array 110 may be adhered to a separate backing, 111. The backing can be flexible or rigid. In some embodiments the backing is an IR-transparent material, e.g. glass, silicon, etc., of from about 150 µm to about 1 mm in thickness, which provides a rigid support for the microneedle array. Exemplary materials include coverslips, microscope slides, and the like. The backing may extend beyond the microneedle array and can be provided with an adhesive to adhere the array to the skin. Shown in FIG. 10B, in some embodiments the backing has one or more elements 112, for example a notch, projection, etc., that provides for ease of handling. Shown in FIG. 10C, the element(s) 112 can also be used to anchor an imaging device 115 or other detection unit, including without limitation a thermal camera, thereby providing stability in the imaging.

The microneedle arrays can comprise dissolving polyvinylpyrrolidone (PVP) microneedles, which microneedles encapsulate biological macromolecules of interest, particularly including allergens. MNs may be fabricated with a wide range of designs (different sizes and shapes).

The microneedles are prepared in the absence of photopolymerization, and do not require adherence to a separately manufactured base. In some embodiments of the invention, the biological macromolecule of interest is an epitopic compound, frequently proteins, peptides, polysaccharides, etc. In some embodiments an array of epitopes are encapsulated in a spatial array of microneedles, for example providing up to 10, up to 100, up to 1000, up to $10^4$, or more epitopes in a single array. By integrating allergen peptides, drugs, and/or polysaccharides within the microneedles in an array, a library of candidate allergens can be tested a single assay.

The dose of macromolecule, e.g. peptide epitope, to be delivered will vary, and may range from at least about 1 ng/microneedle array, at least about 10 ng, at least about 0.1 µg, at least about 1 µg, at least about 10 µg or more in a single microneedle. Typically the polymer from which the microneedles are formed will comprise at least about 100 picograms/ml of the epitopic material, for example a peptide, drug, oligosaccharide, etc., and may comprise up to about 5 mg/ml of epitopic material. The polymer may comprise up to 100 picograms/ml; up to 1 ng/ml, up to 10 ng/ml, up to 100 ng/ml, up to 1 µg/ml, up to 10 µg/ml, up to 100 µg/ml, up to 1 mg/ml, and as much as 5 mg/ml, usually not more than about 3 mg/ml of the epitopic material. The specific dose can be selected based on the allergen in question.

A microarray may comprise a plurality of different allergens, for example a set of common food allergens, a set of pollen allergens, a set of nut allergens, etc. In certain embodiments, the microarray comprises epitopes derived from a plurality of different allergens; other embodiments contemplate that the microarray is composed of epitopes all derived from the same allergen (e.g., a single protein). The microarray is comprised of different allergens that are derived from the same source (e.g., a specific food, e.g., an array of allergens from peanut). In other aspects, the microarray is comprised of different allergens are derived from different sources (e.g., from a group of foods, such as for example, an array of epitopes from allergens from tree nuts for the analysis of allergies to that family of foodstuffs).

An "antigen" refers to any immunogenic moiety or agent, generally a macromolecule, that elicits an immunological response in an individual. Allergens are immunogenic compounds that cause an enhanced Th2-type T cell response and/or IgE B cell response in a susceptible individual. Allergens are commonly proteins, or chemicals bound to proteins, that have the property of being allergenic; however, allergens can also include organic or inorganic materials derived from a variety of man-made or natural sources such as plant materials, metals, ingredients in cosmetics or detergents, latexes, or the like. Pure allergen compositions may be isolated from natural sources, synthesized do novo, prepared by expression from recombinant DNA (see Zeiler et al. (1997) *J Allergy Clin Immunol* 100 (6 Pt 1):721-727), or be obtained by other techniques well-known in the art.

An allergen may comprise multiple epitopes, where each epitope provides a specific binding site for an immunological receptor, e.g. an antibody or T cell receptor. Epitopes may be linear of conformational, and when peptidic in nature can comprise from about one to 10 amino acid residues.

For mapping of epitopes, and array of peptides may be prepared, where such peptides will be at least about 5 or 6 amino acids in length, about 8 amino acids, about 10 amino acids, about 12 amino acids, about 15 amino acids, about 17 amino acids and not more than about 20-25 amino acids in length. Typically a range of about 10 to 20 amino acids is preferred. Overlapping peptides may be generated, where each peptide is frameshifted from 1 to 5 amino acids, thereby generating a set of epitopes. Alternatively a non-overlapping set of contiguous or non-contiguous peptides can be generated.

The epitopes may be sequential from the amino acid structure of the allergen or the epitopes may be non-sequential. In preferred embodiments, it is contemplated that 4, 5, 6, 7, 8, 9, 10, 11, 12, 13, 14, 15, 16, 17, 18, 19, 20, 21, 22, 23, 24, 25, 26, 27, 28, 29, 30, or more sequential or non-sequential epitopes from the same allergen will be provided in an array of microneedles. Each of the epitopes may overlap substantially with at least one other epitope in the array. The size of the epitope and the degree of overlap may be varied according to particular needs using routine experimentation. Multiple epitopes from multiple allergens may be present in any one array.

The compositions and methods of the invention are applicable to a variety of allergens, including food allergens; environmental allergens; animal allergens; etc. Allergens include, e.g. pollens; insect allergens, e.g. bee venom, spider venom, etc.; food allergens, e.g. fish, shellfish (shrimp, crab, lobster, oyster, scallops), soy, strawberries, tree nuts (walnut, hazel/filbert, cashew, pistachio, Brazil, pine nut, almond), peanuts, milk, egg protein, etc.; drug allergens, e.g. penicillin, etc. Insect venoms include, e.g. *Myrmecia pilosula; Apis mellifera* bee venom phospholipase A2 (PLA2) and antigen 5S; phospholipases from the yellow jacket *Vespula maculifrons* and white faced hornet *Dolichovespula maculate*, etc. Pollen allergens may comprise epitopes from a plurality of plants, e.g. birch pollen, ragweed pollen, ParoI (the major allergen of *Parietaria officinalis*) and the cross-reactive allergen ParjI (from *Parietaria judaica*), and other atmospheric pollens including *Olea europaea, Artemisia* sp., *gramineae*, etc.

Allergens of interest for analysis by the methods of the invention include, without limitation, allergens associated with anaphylaxis, which include food allergens, insect allergens and drug allergens. Allergens known to be associated with anaphylaxis include food allergens: peanuts, tree nuts, fish, shellfish, cow's milk, soy, and eggs; insect allergens, particularly from stinging insects, e.g. honeybees, fire ants, yellow jackets, yellow hornets and paper wasps; drugs: β-lactams; nonsteroidal anti-inflammatory drugs (NSAIDs); biologic modifiers, e.g. cetuximab, infliximab and omalizumab. Suitable panels comprising an epitope array from one or more if these allergens are provided.

Other allergens of interest are those responsible for allergic dermatitis caused by blood sucking arthropods, e.g. *Diptera*, including mosquitos (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order Siphonaptera, including the genera *Xenopsylla, Pulex* and *Ctenocephalides felis felis*.

Some specific allergens of interest include egg proteins, which can be provided in a panel of egg protein epitopes from one, two, three, four or more different egg proteins; in combination with a panel of food allergens; etc. Egg allergens include, e.g. Ovomucoid (Gal d1), 210 aa protein; Genbank Accession: P01005.1; Ovalbumin (Gal d2), AltName: Egg Albumin, Plakalbumin, 386 aa protein; Genbank Accession: P01012.2; Ovotransferin (Gal d3), AltName: Conalbumin, Serumtransferrin, 705 aa protein; Genbank Accession: P02789.2; Lysozyme C (Gal d4), AltName: 1,4-beta-N-acetylmuramidase C, 147 aa protein; Genbank Accession: P00698.1; Alpha-livetin (Gal d5), 615 aa protein, Genbank Accession: P19121.2; etc.

Some specific allergens of interest include peanut proteins, which can be provided in a panel of peanut protein epitopes from one, two, three, four or more different peanut proteins; in combination with a panel of food allergens; etc. Peanut allergens include, e.g. Ara h1 (614 a.a); Ara h2.0101 or Ara h2.0201/Conglutin-7/2S albumin(172 a.a)k Ara h3 Glycinin Uniprot O82580; Ara h4 Glycinin seed storage protein Uniprot 5712199; Ara h5 profilin Uniprot Q9SQI9); Ara h6 Conglutin homolog uniprot 5923742; Ara h7 Conglutin homolog uniprot 5923742; Ara h8 Ara h8.0101/PR-10 protein uniprot Q6VT83; Ara h8.0201/PR-10 protein uniprot B0YIU5; Ara h9 Ara h LTP isoallergen precursor; etc.

Some specific allergens of interest include cow's milk proteins, which can be provided in a panel of milk protein epitopes from one, two, three, four or more different milk proteins; in combination with a panel of food allergens; etc. Milk allergens include, Bos Casein βeta-A1 (Uniprot 162797/162805/162931/459292); βeta-A3 Uniprot 459292); αS1 Uniprot 162929; a52; Kappa uniprot 162811, Beta-lactoglobulin; Alpha-lactalbumin, etc.

Some specific allergens of interest include shellfish proteins, which can be provided in a panel of shellfish protein epitopes from one, two, three, four or more different shellfish proteins; in combination with a panel of food allergens; etc. Shellfish allergens include shrimp tropomyosin: Cra c1 accession D7F1J4; Lit v1 accession B4YAH6; Met e1 accession Q25456; Pan b1 accession P86704, Pen a1 accession AAZ76743.1, Pen i1 tropomyosin; shrimp arginine kinase: Cra c2 accession D7F1J5; Lit v2, accession Q004B5; Pen m2, accession E7CGC2; shrimp sarcoplasmic calcium-binding protein: Cra c4, accession D7F1P9; Pen e4; Pen m4 accession E7CGC4; Lit v4 accession C7A639; shrimp myosin light chain: Art fr 5, accession A7L499; Cra c5, accession D7F1Q1; Lit v3, accession B7SNI3, Pen m3, accession E1A683; shrimp troponin C: Pen m6, accession E7CGC5; Cra c6, accession D7F1Q2; triosephosphate isomerase Cra c8, accession D7F1Q0. Crab allergens include tropomyosin: Cha f 1, accession Q9N2R3; Chi o1, accession A2V735; TPM_CHIOP; Can p 1; Eri i 1; Par c 1; Por s 1; Por tr 1; Ran ra 1; Scy o 1, accession A1KYZ3; Scy pa 1; Scy s 1, accession A7L5V2; arginine kinase Chi o2, accession C9EIP1; Scy s 2; Lim p 2 accession P51541; troponin: Chi o 6, accession P86910; Sarcoplasmic calcium-binding protein: Chi o 4, accession P86909. Lobster allergens include tropomyosin: Hom a1 accession 044119.1; Pan s 1 accession O61379.1; arginine kinase: Hom g 2 accession P14208.4; myosin light chain 2: Hom a3 accession EH115965; troponin C: om a6 accession P29291; sarcoplasmic calcium-bindingL Hom a4. Crayfish allergens include tropomyosin: Pro cl i accession ACN87223.1; sarcoplasmic calcium-binding protein: Pon I4 accession P05946; troponin I: Pon 17 accession P05547. Krill allergens include tropomyosin: Eup p1 accession BAF76431.1; Eup s 1 accession dbj|BAF95205.1. Mollusk allergens include tropomyosin: Hel as 1 accession CAB38044; Hal a 1 accession AAP85231.1; Tod p 1 accession Q9BLG0.3; hemocyanin: Meg C accession CAG28309.2; paramyosin: Hal di accession BAJ61596.1; Myt g accession BAA36517.1; Oct v; Tur c; Hal r.

Some specific allergens of interest include soy proteins, which can be provided in a panel of soy protein epitopes from one, two, three, four or more different soy proteins; in combination with a panel of food allergens; etc. Soy allergens include Gly m 5 Glycine Beta-conglycinin accession CAA35691.1; Gly m 5 Glycine Beta-conglycinin accession AAA33947.1; Gly m 5 Glycine Beta-conglycinin accession AAB01374.1; Gly m 5 Glycine Beta-conglycinin accession AAB23463.1; Glycine Gly m 1 accession AAB34755.1; Glycine Gly m 1 accession ABA54898.1; Glycine Gly m 3 accession CAA11755.1; Glycine Gly m 3 accession 065809.1; Glycine Gly m 3 accession ABU97472.1; Glycine Gly m 4 accession P26987.1; Glycine Gly m 8 2 s albumin accession AAD09630.1; Glycine Gly m Bd 28K accession BAB21619.1; Glycine Gly m Bd 28K accession ACD36976.1; Glycine Gly m Bd 28K accession ACD36975.1; Glycine Gly m Bd 28K accession ACD36974.1; Glycine Gly m Bd 28K accession ACD36978.1; Glycine Gly m Bd accession P22895.1; Glycine Gly m Bd accession AAB09252.1; Glycine Gly m Bd accession BAA25899.1; Glycine Glycinin G1 accession CAA26723.1; Glycine Glycinin G1 accession CAA33215.1; Glycine Glycinin G2 accession CAA26575.1; Glycine Glycinin G2 accession CAA33216.1; Glycine Glycinin G3 accession CAA33217.1; Glycine Glycinin G4 accession CAA37044.1; Glycine Glycinin G5 accession AAA33964.1; Glycine Glycinin G5 accession AAA33965.1; Glycine Major Gly 50 kDa allergen accession P82947.1; Glycine Trypsin inhibitor accession AAB23464.1; Glycine Trypsin inhibitor accession AAB23482.1; Glycine Trypsin inhibitor accession AAB23483.1; Glycine Trypsin inhibitor accession CAA56343.1; Glycine Glycinin G4 accession CAA60533.1; Glycine Glycinin G5 accession CAA55977.1.

Some specific allergens of interest include tree nut proteins, which can be provided in a panel of tree nut protein epitopes from one, two, three, four or more different tree nut proteins; in combination with a panel of food allergens; etc. Tree nut allergens include Almonds: Pru du 3/Pru du 3.0101 (123 aa) Accession: ACN11576s/GI:223667948; Pru du 4 Accession: AAL91664/GI:24473798; Pru du 5/Pru du 5.0101 Accession: ABH03379/GI:111013714; Pru du 6/Amandin Accession: ADN39440/GI:307159112; Chain A, Amandin (531 aa)-Accession: 3EHK_A/GI:258588247; Chain B, Amandin (531 aa)-Accession: 3EHK_B/GI:258588248; Chain C, Amandin (531 aa)-Accession: 3EHK_C/GI:258588249; Prunin 2 precursor/Pru du 6.0201, Accession: ADN39441/GI:307159114; Putative Pru du 6 Accession: AGR27935/GI:523916668. Walnuts: Jug n1 Accession: AAM54365/GI:31321942 or AAB41308/GI:1794252; Jug n2 Vicillin seed storage protein (481 aa)-Accession: AAM54366/GI:31321944; Jug r1 Albumin Seed Storage, Accession: AAB41308/GI:1794252; Jug r2 Accession: AAF 18269/GI:6580762; Jug r3; Jug r4 Accession: AAW29810/GI:56788031. Cashews: Ana o1 accession: AAM73730/GI:21914823; Ana o2 Accession: AAN76862/GI:25991543; Ana o3 Accession:AAL91665.1 GI:24473800. Chestnuts: Cas s1 Accession: CAD10374/GI:16555781; Cas s5 Accession: Q42428/GI:75282355; Chitinase isoform 2 Accession: ADN39439/GI:307159110; Endochitinase Accession: P29137/GI:116301; Cas s8; Cas s9 Accession: CAE46905/GI:46359518. Pecans: Car i1 Accession: AAO32314/GI:28207731; Car i4 Accession: ABW86978/GI:158998780; Accession: ABW86979/GI:158998782. Hazelnuts: Cor a 1 Accession: CAA50327/GI:22688; Cor a 1.0102 (161 aa)-Accession: CAA50328/GI:22690; Cor a 1.0103 (161 aa)-Accession: CAA50325/GI:22684; Cor a 1.0104 (161 aa)-Accession: CAA50326/GI:22686; Cor a 1.0201 (161 aa)-Accession: CAA96548/GI:1321731; Cor a 1.0301 (161 aa)-Accession: CAA96549/GI:1321733; Cor a 1.0401 (161 aa)-Accession: AAD4840/GI:5726304; Cor a 1.0402 (161 aa)-Accession: AAG40329/GI:11762102; Cor a 1.0403 (161 aa)-Accession: AAG40330/GI:11762104; Cor a 1.0404 (161 aa)-Accession: AAG40331/GI:11762106 Cor a 10 Accession: CAC14168/GI:10944737; Cor a 11 Accession: AAL86739/GI:19338630; Cor a 12/oleosin Accession: AAO67349/GI:49617323; Cor a 13/oleosin Accession: AAO65960/GI:29170509; Cor a 14/2S albumin Accession: ACO56333/GI:226437844; Cor a2 Accession: AAK01235/GI:12659206; Cor a8 Accession: AAK28533/GI:13507262; Cor a9 Accession: AAL73404/GI:18479082. Pistachio: Pis v1 Accession: ABG73108/GI:110349081; Pis v2 Accession: ABG73109/GI:110349083; Pis v2.0201/11S globulin precursor ABG73110/GI:110349085, Accession: ABU42022/GI:156001070; Pis v3; Accession: ABO36677/GI:133711974; Pis v4 Accession:ABR29644/GI:149786150; Pis v5 Accession: ACB55490/GI:171853010.

Some specific allergens of interest include wheat proteins, which can be provided in a panel of wheat protein epitopes from one, two, three, four or more different wheat proteins; in combination with a panel of food allergens; etc. Wheat allergens include Profilin (Tri a 12); Tri a 12.0101 accession P49232; Tri a 12.0102 accession P49233; Tri a 12.0103 accession P49234; Tri a 12.0104 accession B6EF35; Tri a 14.0201 accession D2T2K2; Tri a 15.0101 accession D2TGC3; Tri a 18.0101 accession P10968; Tri a 19.0101; Tri a 21.0101 accession D2T2K3; Tri a 25.0101 accession Q9LDX4; Tri a 26.0101 accession P10388; Tri a 26.0201 accession Q45R38; Tri a 27.0101 accession Q7Y1Z2; Tri a 28.0101 accession Q4WOV7; Tri a 29.0101 accession C7C4X0; Tri a 29.0201 accession D2TGC2; Tri a 30.0101 accession P17314; Tri a 31.0101 accession Q9FS79; Tri a 32.0101 accession Q6W8Q2; Tri a 33.0101 accession Q9ST57; Tri a 34.0101 accession C7C4X1; Tri a 35.0101 accession D2TE72; Tri a 36.0101 accession 335331566; Tri a 37.0101 accession Q9T0P1; Tri a 39.0101 accession J7QW61.

Allergen immunotherapy, or hyposensitization is the parenteral administration of allergenic extracts as antigens at periodic intervals, usually on an increasing dosage scale to a dosage that is maintained as maintenance therapy. Allergen immunotherapy may be indicated for a patient that is shown to have a strong allergic response to an allergen by the methods of the invention. Indications for immunotherapy are determined by appropriate diagnostic procedures coordinated with clinical judgment and knowledge of the patient history of allergic disease. Allergen immunotherapy is performed by providing injections of the allergen to the allergic subject on a regular basis, with the goal of reducing the symptoms and signs of an allergic reaction or prevention of future anaphylaxis against antigens such as insect venom, penicillin, etc. This is usually done initially with low doses, with gradual dosage increases over a period of weeks.

The amount of allergen to be injected may be empirically derived, and will depend on the size of the recipient, usually at least about 100 ng allergen/kilogram of body weight, and not more than about 1 mg allergen/kilogram body weight. Frequently the dose will be increased through the course of injections by as much as about ten to one hundred fold. Injection schedules vary with individual patients. For example, Allpyral preparations are administered every 1-2 weeks until a maintenance dose is reached. Maintenance injections are administered every 2-4 weeks. It should be re-emphasized that immunotherapy schedules are individualized and fixed schedules are not recommended, particularly when aqueous extracts are used. Allergy injections rarely go on "forever" but can usually be stopped after a patient has experienced no allergic symptoms and has required no medication for 18-24 consecutive months while on the maintenance schedule. Duration of treatment for the average patient is 3 to 5 years but could be longer in certain clinical settings. If symptoms recur after a 6 to 12 months observation period following discontinuation of immunotherapy, re-evaluation is warranted.

Allergen immunotherapy may be appropriate for the following indications: Severe, seasonal (lasting 2 or more years) or perennial, IgE-dependent allergic rhinoconjunctivitis in which optimal allergen avoidance and medication have not been sufficiently effective in controlling symptoms. IgE-mediated allergic asthma; particularly where there is a clear temporal association between exposure to the allergen and signs and symptoms of asthma, and those in which symptoms have occurred during two or more allergy seasons in successive years. IgE-mediated asthma caused by house dust mites or ragweed pollen may be treated with allergen immunotherapy. IgE-mediated anaphylactic reactions to insect stings. Immunotherapy with venom from yellow jackets, yellow hornets, white-faced hornets, wasps and honey-bees, and with whole-body extracts of fire-ants, is effective.

Methods of Determining Allergen Sensitivity

Methods of the invention can be used to confirm the presence of immediate-type hypersensitivity to allergens suspected from an individual's history or to confirm allergies to commonly encountered allergens such as pollens, grasses, insects, molds, antibiotics, and a variety of foods; to determine whether environmental allergens are indicated in chronic or persistent cases of asthma, rhinorrhea, bronchospasm, urticaria, eczema, or anaphylaxis; or to document immediate hypersensitivity prior to conducting other allergy testing, such as provocation testing (bronchial provocation, oral food provocation), or prior to allergy desensitization therapy.

A microneedle array, including without limitation a dissolving microneedle array as described herein, comprising one or more epitopes of macromolecules, particularly proteins and more particularly peptides derived therefrom, is brought into contact with the skin of the individual to be tested and pressed down into the skin, so as to deliver the epitopes to the intradermal space. The array may be adhered to a backing so as to securely position to the skin. A backing of interest can be a rigid or flexible support. For some embodiments of the invention, the backing is transparent to ultraviolet radiation, e.g. a glass slide or coverslip. Following delivery, the microneedles deliver the protein and/or peptides to the intradermal space, where an immune response will be generated in an allergic individual. In some embodiments of the invention, the backing is removed for an analysis of responsiveness. In other embodiments, the backing is not removed for an analysis of responsiveness.

If the individual being tested has an allergic response to one or more epitopes present on the microarray, the skin will respond rapidly, typically within no more than about 15 minutes, by release of histamine, mast cell degranulation, etc. The response can be detected visually or thermally. In some embodiments, one or more images are captured at the site where the array has penetrated the skin, e.g. a visual image, for example reddening of the injection site, a thermal image, and the like. Images can be captured at one or more time points following microneedle injection, e.g. within about 10 seconds, within about 30 seconds, within about 60 seconds, within about 2 minutes, 3 minutes, 4 minutes, 5 minutes, and up to 10 minutes, up to 15 minutes, etc.

Each of the captured images can be analyzed to assess the degree of reaction over the array of epitopes, and to generate a report of the information to be provided to the individual. In some embodiments the images are captured with a camera in visible light. In other embodiments, the image capture is performed with a thermal camera, where an increase of heat in the skin is detected at the point where an allergen is present. A camera may be secured to the individual, secured to the backing of the array, aligned with a fixed point of reference, and the like.

Thermal imaging can be used to visualize and quantify temperature changes on the skin surface in response to the application of food allergen patches comprising linear peptide epitopes. The images are captured using an infrared thermal image camera, including without limitation ICI 7320 P-series camera which has FDA 510K clearance that meets or exceeds the needs for all medical thermal imaging infrared applications in clinical settings. This is an uncooled, UFPA camera that uses radiometric microbolometer imager with Vanadium Oxide detector (VOx) to capture infrared energy in the 2.6 to 25 micrometer spectrum. It is a camera with 320×240 resolution and a video refresh rate of 50-60 Hz. It has a 16-bits temperature dynamic range that can measure temperature from −20 degree Celsius to 100 Celsius with accuracy of +/−1 degree Celsius and thermal sensitivity of about 0.027 Celsius. This camera is equipped with 10 mm manual lens with 46 degree FOV (Field of View) and focusing distance of 4 inches to infinity.

The thermal signal of each spot can be captured using an infrared thermal image camera and transformed into a score. Each score is calculated by subtracting the mean score of negative controls analyzed in the same patch. For each spot, the continuous responses of adjacent spots can be measured and used to normalize responses. Furthermore, baseline differences in the pre-test temperatures of the skin can be used for normalization. The response for each peptide can be compared against population-wide responses, which had been pre-determined to establish a threshold level. An individual peptide is considered positive if the score is greater than threshold (=1 SD over baseline). The kinetics of response for each peptide can also be measured. Kinetic responses that are judged to be rapid by comparison to population-wide controls can also be scored as positive.

An algorithm is optionally applied in the analysis, which algorithm can include the assessment of one or more parameters including, without limitation, the degree of response, e.g. heat or reddening, the speed of response, the number of epitopes that elicit a response, the percent of epitopes in a given protein that elicit a response, the number of related proteins containing epitopes that elicit a response, weighting of a response to epitopes that are associated with more severe or less severe allergies; and the like.

In some embodiments a bioinformatics method is provided for that selection of epitopes, e.g. peptides, with the improved accuracy for classifying clinically relevant allergic responses. An algorithm incorporates an analysis of epitopes relevant to a determination of severity and/or persistence of an allergic reaction. Such an algorithm is useful in determination weighting of epitopes when assessing an individual response. Parameters of interest include one or more of: proportion of epitopes that elicit a positive response; threshold number of epitopes that elicit a positive response; speed of response; kinetics of response; absolute level of thermal or visual response; etc.

A factor in the weighting of responses is the presence of cross-reactivity. A severe allergy to pollen can indicate that an individual may be susceptible to developing the oral allergy syndrome or anaphylaxis when eating certain foods. Such reactions are due to profilins, homologous proteins found both in pollens and plants and fruits. Oral allergy syndrome also has been reported following ingestion of crustaceans by individuals who are sensitive to house dust mites. Examples of cross reactivity associations include:

Inhalant Allergen Food Allergens
Birch pollen Apple, raw potato, carrot, celery, hazelnut, pear, peach, plum, cherry
Mugwort pollen Celery, apple, peanut, kiwi fruit, carrot, parsley, spices (fennel, coriander, aniseed, cumin)
Ragweed pollen Melons, e.g., watermelon, cantaloupe, and honeydew, bananas
Latex Avocado, kiwi fruit, chestnut, papaya, banana
Chironomidae Crustaceans (shellfish)

Also provided are databases of allergen responsiveness profiles. Such databases can typically comprise results derived from various individual conditions, such as individuals having drug allergies, known anaphylactic responses, etc. The results and databases thereof may be provided in a variety of media to facilitate their use. "Media" refers to a manufacture that contains the allergen response information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test responses.

A scaled approach may also be taken to the data analysis. For example, Pearson correlation of the profile results can provide a quantitative score reflecting the signature for each sample. The higher the correlation value, the more the sample resembles a reference profile. A negative correlation value indicates the opposite behavior. The threshold for the classification can be moved up or down from zero depending on the clinical goal.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5118-21, herein incorporated by reference). The set of null distribution is obtained by: permuting the values of each profile for all available profiles; calculating the pairwise correlation coefficients for all profile results; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying any of the datasets and data comparisons of this invention. Such data may be used for. a variety of purposes, such as drug discovery, analysis of interactions between cellular components, and the like. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output tests datasets possessing varying degrees of similarity to a trusted profile. Such presentation provides a skilled artisan with a ranking of similarities and identifies the degree of similarity contained in the test profile.

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data (e.g., allergen response results), can be input into a computer by a user either directly or indirectly. Additionally, any of the devices which can be used to sequence DNA or analyze DNA or analyze allergen response data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location.

Methods of Producing Microneedle Array

For the purposes of the present invention, the microneedles are formed from a polymer array mixture in which the biodegradable material PVP is mixed with PEG and the biological macromolecule of interest, e.g. allergen, that is to be delivered. The dose of macromolecule to be delivered will vary, and may range from at least about 1 ng/microneedle array, at least about 10 ng, at least about 0.1 µg, at least about 1 µg, at least about 10 µg or more per $cm^2$ of a single array. MNs may be fabricated with a wide range of designs (different sizes and shapes).

To accurately produce the micro-scale dimensions of polymer MNs, a variety of mold-based techniques, such as casting, hot embossing, injection molding, and investment molding may be used, e.g. beveled-tip, chisel-tip, and tapered-cone polydimethylsiloxane (PDMS) molds. For example, to fabricate a mold, a silicon wafer with oxide mask can be patterned using standard contact lithographic techniques using thick photoresist and subjected to deep reactive ion etching. Residual photoresist is removed and the wafers washed in sulfuric acid. To facilitate easy removal of molded materials, the wafers can be silanized. To prepare PDMS molds, PDMS monomer and curing agent are mixed and poured onto Si-wafers, and incubated to allow curing.

As shown in FIG. 10A, the microneedle array comprises a planar surface 114, and multiple needle projections 113. The array is formed by casting in a mold 130, particularly a PDMS mold, which has a planar surface 134 and wells 133. The planar surface 134 can be patterned 135 with grooves or microscale protrusions to provide for a so-called "petal effect" (superhydrophobicity with high droplet adhesion). Microdimple structures display lotus leaf-like superhydrophobicity, while the complex protrusions produce size-selective water droplet adhesion, owing to van der Waals' forces at the water contact area. The patterning of the surface provides for improved separation during spotting of individual epitopes into microneedles, such that the epitopic material is contained within a single microneedle or a small patch of microneedles. Methods of patterning PDMS are known in the art, for example periodic line-patterned polydimethylsiloxane (PDMS) surfaces are created by laser. See, for example, Ma et al. *Current Opinion in Colloid & Interface Science* 11.4 (2006): 193-202; Truesdell, et al. Physical review letters 97.4 (2006): 044504; Cortese, et al. "Superhydrophobicity due to the hierarchical scale roughness of PDMS surfaces." *Langmuir* 24.6 (2008): 2712-2718; etc., herein specifically incorporated by reference.

In the polymer array mixture, PVP can be dissolved in an aqueous or ethanolic solution, at a concentration of at least 25 mg/ml, at least 50 mg/ml and not more than about 250 mg/ml, usually not more than about 100 mg/ml. PEG, e.g. PEG100, PEG200, PEG400, PEG1000, etc. is used as a plasticizer, in the absence of a photocrosslinking agent. PEG is added at a concentration of from about 1:1000 v/v to not more than about 25:1000, usually not more than about 15:1000, or 10:1000 and can be effective at around about 5:1000 v/v. The pH can be adjusted if required.

The biological macromolecule is added to the PVP mixture at a concentration that will provide an effective dose once penetrated to the skin, usually at least about 0.01% w/w of PVP, at least about 0.1% w/w of PVP, at least about 1% w/w PVP, and not more than about 5% w/w PVP. Where the allergen is a peptide epitope, it can be added at a concentration of up to 100 picograms/ml; up to 1 ng/ml, up to 10 ng/ml, up to 100 ng/ml, up to 1 µg/ml, up to 10 µg/ml, up to 100 µg/ml, up to 1 mg/ml, and as much as 5 mg/ml, usually not more than about 3 mg/ml. It will be appreciated that a balance needs to be reached between the dose that is required to elicit a response, and the dose that may create an undesirable adverse immune response, and thus the specific dose can be dependent on the allergen. A control is generally included, where a negative control can be, without limitation, the PVP mixture free of peptides or containing non-allergenic compounds. A positive control may be a biological activator, e.g. histamine, etc., a known allergen, and the like.

Peptides can be prepared from a variety of synthetic or enzymatic schemes, which are well known in the art. Where short peptides are desired, such peptides are prepared using automated peptide synthesis in solution or on a solid support in accordance with conventional techniques. Various automatic synthesizers are commercially available and are used in accordance with known protocols. Numerous other documents teaching solid phase synthesis of peptides are known to those of skill in the art and may be used to synthesize epitope arrays from any allergen. The peptides also may be modified, and such modifications may be carried out on the synthesizer with minor modifications. An amide could be added at the C-terminus of the peptide. An acetyl group could be added to the N-terminus. Biotin, stearate and other modifications could also be added to the N-terminus.

Optionally saccharides are included in the polymer array mixture for improved strength and stability. Saccharides are included as a concentration of from about 1% w/w, from about 2% w/w from about 3% w/w, up to about 10% w/w, up to about 8% w/w, and may be around about 2%, 3%, 4%, 5%, 6%, 7%, 8% of the polymer array mixture. Suitable saccharides include, without limitation, mono- and di-saccharides, e.g. trehalose, sucrose, lactose, maltose, etc.

This mixture is cast in the PDMS molds, for example by patterning the set of epitopic compounds in an array and dispensing droplets to wells of the mold. The mold containing the PVP mixtures is placed in a vacuum chamber to remove air from the needle channels. The needles are dried for a period of from about 12-36 hours, and are then peeled from the mold, and can be stored in a dessicator. As the polymer solution dries, PVP fibrils and optionally saccharides, are deposited on the periphery of the drying solution, resulting in encapsulation of the intact and biologically active macromolecule in a microneedle that rapidly dissolves upon exposure to a fluid environment, for example following deposition in the skin.

Systems and Kits

In other embodiments of the invention, an article of manufacture containing a microneedle array of the invention is provided. Such an article of manufacture may include a microneedle array, as described herein. The microneedle array may be loaded with an effective dose of allergenic peptides of the invention.

In some embodiments an allergy testing system is provided. The allergy testing system includes a microneedle array, e.g. a dissolving microneedle array, wherein an array of epitopes are encapsulated in the spatial array of microneedles, for example providing up to 10, up to 100, up to 1000, up to $10^4$, or more epitopes in a single array. The allergy testing system may further comprise a suitable backing to adhere the microneedle array to the skin. The system may optionally comprise a device for imaging, including a visual or thermal camera, and imaging software for analysis of responsiveness to the epitope array. The device for imaging may be operably connected to a data processing unit, e.g. with a wired or wireless connection.

In some embodiments a kit is provided for use in the system, where a kit comprises a microneedle array comprising one or a panel of allergens, as described herein. Sets of allergens may include, without limitation, environmental allergens; insect allergens; food allergens; drug allergens, etc.

The article of manufacture may comprise a container and a label. Suitable containers include, for example, plates, bottles, vials, tubes, etc. The containers may be formed from a variety of materials such as glass or plastic. The label on, or associated with, the container indicates that the composition is used for a method of interest. The article of manufacture may further include other materials desirable from a commercial and user standpoint, including other buffers, diluents, filters, needles, syringes, and package inserts with instructions for use.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

A method of preparing PVP microneedles that results in the intact delivery of proteins to the skin is provided, which method is superior to the photopolymerization method. Non-covalently aggregated polymers such as PVP hold high promise for the development of smart drug delivery materials because of their biocompatibility and low manufacturing cost. Here we use the self-assembling properties of polyvinylpyrrolidone (PVP) in aqueous and alcoholic solutions to make microneedles. We demonstrate that these protein-encapsulated polymer microneedles are able to deliver proteins to the human intradermal space effectively. These microneedles dissolve once inserted, eliminating the need for disposal of hazardous, sharp needles after administration. By integrating allergen proteins within the microneedles in an array, a library of allergenic proteins or their component peptides are tested in a single assay, and this concept is demonstrated in a multi-allergen patch.

Materials and Methods

Preparation of Labeled Proteins.

Peanut flour was obtained from the Golden Peanut Company (Alpharetta, Ga.). Peanut flour was mixed with water and dissolved by sonication in a water bath for 15 min. To remove insoluble components and separate out the protein, the mixture was centrifuged at 3,000×g for 10 min. The middle layer of the supernatant containing soluble peanut proteins was collected with a syringe, discarding the top layer of the supernatant since it comprised fats and oil. The middle layer of the supernatant was further centrifuged at 18,000×g for 10 min and the pellet, containing insoluble components, was discarded.

The protein content in the supernatant was measured by bicinchoninic acid assay (BCA). The protein was then lyophilized and labeled with rhodamine using 1-Ethyl-3-(3-dimethylaminopropyl) carbodiimide (EDC) and N hydroxysulfosuccinimide (Sulfo-NHS) as the cross-linkers. Briefly, 3.25 mg 5(6) carboxytetramethylrhodamine (Sigma-Aldrich, Steinheim, Germany), 3.3 mg EDC (Thermo Scientific, Rockford, Ill.) and 2.9 mg Sulfo-NHS (ChemPep, Wellington, Fla.) were mixed and stirred for 1 hr in 1 mL MES buffer (pH 6.0). 20 mg of peanut protein in 5 mL MES buffer was added and stirred at 4° C. in dark overnight. The mixture was then purified by using either Slide-A-Lyzer dialysis cassette G2 (3,000 MWCO, Thermo Scientific, Rockford, Ill.) in MES buffer or centrifugal filter devices (3,000 MWCO, Millipore, Billerica, Mass.). The completeness of the dialysis was confirmed by checking the fluorescence of the wash. The labeled peanut protein was lyophilized and stored at −80° C. until use.

To label casein protein, 43 mg of casein from bovine milk (Sigma-Aldrich, Steinheim, Germany) was dissolved in 2.85 mL of 0.1 M $NaHCO_3$ (pH 9.5). 1.8 mg of rhodamin B isothiocyanate (RBITC) (Sigma-Aldrich, Steinheim, Germany) dissolved in 150 µL of dimethyl sulfoxide (DMSO) (anhydrous) was added dropwise into the casein solution while stirring. The mixture was stirred for 2 h at room temperature in the dark. Labeled casein (RBITC-casein) was purified on a PD-10 desalting column (GE Healthcare Life Sciences, Pittsburgh, Pa.) equilibrated with $H_2O$ (pH adjusted to 8.5 using 1 N NaOH). Purified RBITC-casein was stored at 4° C. or used immediately to prepare microneedles. DQ ovalbumin was obtained from Invitrogen.

Preparation of streptavidin (SA) PVP microneedles followed a similar scheme to other microneedles. To begin, 5 mg SA lyophilized powder (ImmunoPure Streptavidin, Pierce/Thermo Scientific) was reconstituted by dissolving in 0.5 mL $H_2O$. To prepare the SA PVP microneedles, 100 mg of PVP (10 kDa) was dissolved in 1.9 mL of $H_2O$ and mixed with 7.5 µL of PEG400 and 0.1 mL of 10 mg/mL reconstituted SA. This mixture was cast in the PDMS molds and placed in a vacuum chamber to remove air from the needle channels. The needles were left to dry on the bench top and peeled free from the mold after 24-36 h.

Photochemically crosslinked PVP microneedles were prepared by mixing 1-vinyl-2-pyrrolidone and 2,2'-Azo bis(2-methylpropionitrile) (10:1 w/w) with and without streptavidin (1% w/w). The mixture was used to cast the PDMS molds. Vacuum was applied to remove the air from the needle channels. The needles were irradiated with UV-light overnight and peeled from the molds.

Preparation of Polydimethylsiloxane (PDMS) Mold.

To fabricate the mold for our microneedles, a silicon wafer with oxide mask was patterned using standard contact lithographic techniques using thick photoresist and subjected to deep reactive ion etching. Residual photoresist was removed using oxygen plasma and the wafers were washed in sulfuric acid. To facilitate easy removal of molded materials, all wafers were silanized overnight in a vacuum chamber prior to use. To prepare PDMS molds, PDMS monomer and curing agent (10:1 w/w, Dow Corning, Midland, Mich.) were mixed and poured onto Si-wafers in a sterile Petri dish. To remove bubbles of trapped air, vacuum was applied for 20-30 min and the Petri dishes were gently rapped. To cure the PDMS, the Petri dish was incubated at 37° C. overnight.

Preparation of Allergen Microneedles.

To form polyvinylpyrrolidone (PVP)-based biodegradable microneedles incorporating labeled-proteins, we dissolved 200 mg PVP (10 k MW, Sigma-Aldrich, USA) in 3.4 mL ethanol (EtOH) and 15 µL plasticizer (polyethylene glycol-400). Labeled protein (2 mg, 1% wt of PVP) was dissolved and sonicated in 100 µL water to obtain a clear solution, then added to the PVP-EtOH mixture. We adjusted the pH to 8-8.5 (for casein) or 9-10 (for peanut protein) by titrating 0.1 N NaOH until the mixture was clear. For the DQ ovalbumin microneedles, EtOH was replaced by deionized water to avoid precipitation of the protein. The PVP-protein mixture was poured onto PDMS molds. Vacuum was applied to force out trapped air in the needle channels of the molds. The molds were left in a fume hood to evaporate the solvent (EtOH or water). The dried microneedles were carefully peeled from the mold and stored in a desiccator.

Photochemical crosslinked PVP microneedles were prepared by mixing 1-vinyl-2-pyrrolidone and 2,2'-Azobis(2-methylpropionitrile) (with and without proteins), poured onto PDMS molds. Trapped air was removed under vacuum and then irradiated with UV-light overnight. The cross-linked microneedles were peeled and stored in desiccator.

Streptavidin Binding Activity Using Biotin Quantitation Assay.

The binding activity of SA in the microneedles was analyzed by measuring the unbound biotin present after incubating it with biotin horseradish peroxidase (biotin-HRP). The SA-PVP microneedles were dissolved in $H_2O$ to the final concentration of 3.33 mg/mL of SA and 330 mg/mL of PVP. Dissolved SA-PVP microneedles or a mixture of PVP+SA (weight ratio same as in microneedles) were treated with 5 mg/mL biotin-HRP and incubated at room temperature for 2 h. Free biotin was measured using the biotin quantitation kit (Thermo Scientific, Rockford, Ill.) according to the manufacturer's instruction. Briefly, 10 µL HABA (4'-hydroxyazobenzene-2-carboxylic acid)/avidin was mixed with 80 µL 1×PBS. 10 µL of the pre-mixture of SA-biotin-HRP was then added to the solution and incubated at room temperature for 30 min. Absorbance at 500 nm, reflecting displacement of HABA from the SA, was measured using a NanoDrop 2000 (Thermo Scientific, Rockford, Ill.). To determine the total biotin input, a control solution contained only biotin-HRP. PVP or SA alone was also tested using the same method as control samples. For SDS-PAGE experiments, the PVP-SA microneedle solution was mixed within sample buffer (NuPage, Life Technologies, Carlsbad, Calif.). The mixture (containing ~10 µg of SA) was loaded into the well and fractionated by using 10% Bis-Tris SDS-PAGE gels (1.0 mm×10 well) (NuPage) and then stained using a Coomassie staining kit (NuPage).

Skin Penetration and Microscopic Examination of Fluorescence.

Human foreskin was obtained from discarded neonatal foreskins obtained after elective circumcision. Institutional Review Board (IRB) approval was obtained prior to tissue collection. The sample was cut into a ~1 cm×1 cm square and pinned onto a Styrofoam board with epidermis facing up. A small patch of fluorescently labeled microneedles (~0.5 cm×0.5 cm) was applied onto the skin and secured in place with a Tegaderm. The microneedles were pressed down using a small Petri dish for 30 s. After 5 min, the Tegaderm was removed and the skin was gently stripped with another clean Tegaderm to remove any residues on the surface. Still pinned on the sytrofoam, the skin was immersed in 4% paraformaldehyde and fixed overnight. Fixed skin was embedded in optimum cutting temperature (O.C.T.) formulation on dry ice and cryosectioned. Tissue slides were preserved in mounting medium with DAPI (4',6-diamidino-2-phenylindole) (Vector Labs) and examined by widefield fluorescence microscopy. Fluorescence intensity was quantified using ImageJ.

Scanning Electron Microscopy Characterization.

The morphology of the microneedles was characterized using scanning electron microscopy (SEM). The microneedles along with their bases were attached to an SEM sample stub using a double-stick carbon tab. The samples were coated with a 7 nm thick Au-Palladium layer using a Denton Desk II vacuum sputter coater. Imaging was carried out on a Hitachi S-3400N VP scanning electron microscope at the Cell Sciences Imaging Facility (CSIF), Stanford University.

Coating Steel Microneedles.

AdminPatch array 1500 steel microneedles (AdminMed) were dip-coated using a standard technique. Briefly, a coating solution formulated with 1% (w/v) carboxymethylcellulose (Aquacide II, EMD Millipore), 0.5% (w/v) Poloxamer 188, 15% (w/v) sucrose (Sigma) and 0.5% (w/v) rhodamine B labeled casein. Skin penetration tests were performed immediately after coating using the procedure described for polymer microneedles.

Results and Discussion

Physical Characteristics of Fluorescent Labeled Allergen Microneedles.

Microneedles were prepared as described containing various proteins that were labeled with a fluorophor. After the microneedles were peeled from the mold, we imaged them using wide field microscopy (FIG. 1A). The microneedles were of consistent shape and spacing, regardless of the protein constituent, and reflected the dimensions of the mold. The measured dimensions showed a height of approximately 400 μm and spacing of 500 μm, center to center (FIG. 1B).

Figure 2B:
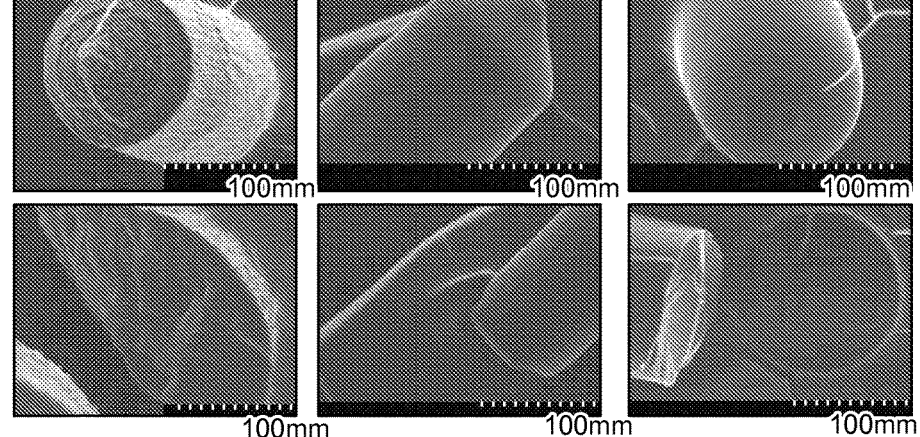
Figure 2C:
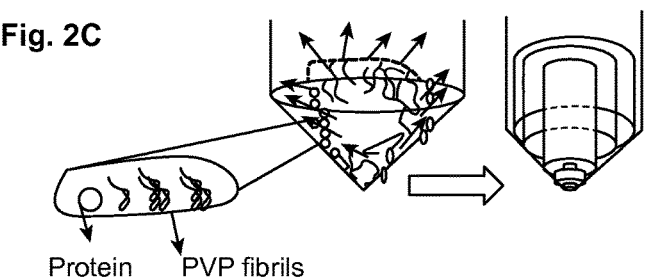

To further characterize the microneedles, the structures were examined using scanning electron microscopy (SEM) (FIG. 2A). The PVP/casein microneedles had a rugged texture, in contrast to the smoother texture of PVP/peanut protein and control PVP microneedles. These features could reflect different arrangements of the incorporated proteins within the matrix of PVP fibers. To study the structure of the interior of the microneedles, they were broken and visualized by SEM. We found that the interior of the needles was uniform with some hints of concentric circular features (FIG. 2B middle, also seen in FIG. 3), indicating orderly self-assembly of molecules as shown in the schematic representation (FIG. 2C).

These results demonstrate the surface and interior textures of PVP microneedles incorporating allergen proteins and control PVP microneedles. Upon drying, concentrated PVP solution developed into concentric fibrous PVP structures. This is due to the "coffee drying effect" originally demonstrated by in explaining a polymer solution drying on a planar surface (see Deegan et al. (1997) Nature 389:827-9; Kuncicky and Velev (2007) Langmuir 24:1371-80). We found this effect operating in the drying process when the polymer solution was poured into the PDMS templates. As the polymer solution dried, the PVP fibrils are deposited on the periphery of the drying solution, as was next studied by fluorescence microscopy.

Figure 3C:
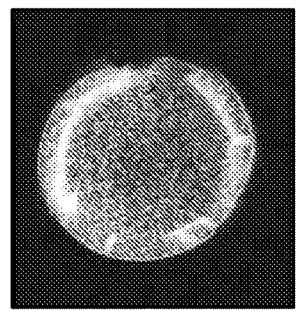
FIG. 3A-3D Confocal images of PVP-protein microneedle.
Figure 3B:
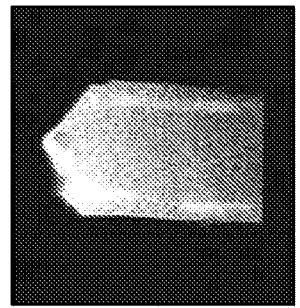
Figure 3D:
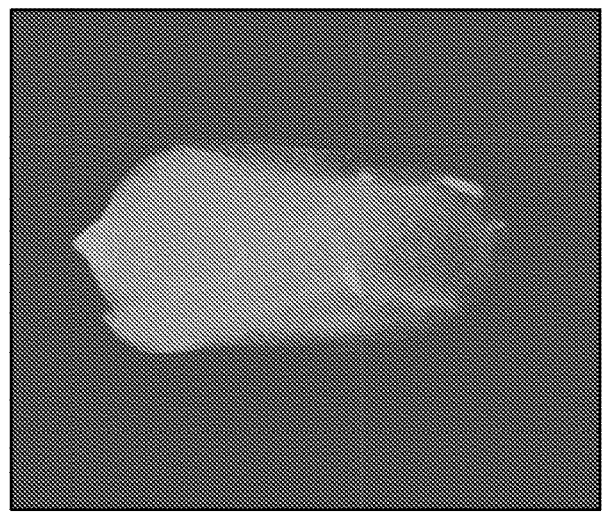
Figure 3A:
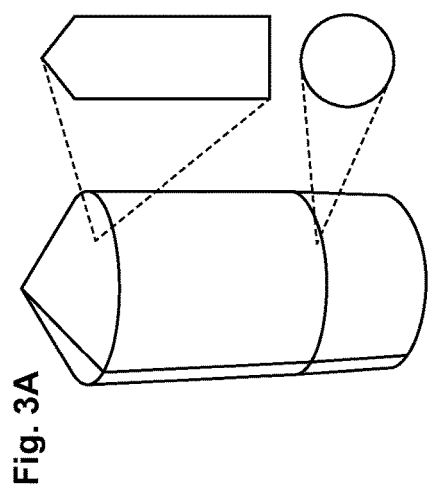

To study the distribution of allergen proteins inside the microneedles, labeled microneedles were secured in embedding resin and imaged by fluorescence confocal microscopy. Optical sections of the microneedles showed that fluorescently labeled allergen proteins were distributed throughout the microneedle (schematically illustrated in FIG. 3A). Notably, the distribution was not uniform. A concentrated, subsurface layer of protein was found in the needles (FIG. 3B), with a partial ring-like structure observed in the horizontal cross section (FIG. 3C). Areas of concentrated proteins were also found along the cylindrical axis of the needle (FIG. 3D). This is consistent with our interpretation of coffee drying phenomenon, which noted separation of heteromeric aggregates during the drying process, in explaining the internal structure of our microneedles. Presumably PVP-proteins formed smaller fibers or aggregates as compared to plain PVP aggregates. The cone angle of the microneedle was measured to be ~49 degrees, which is consistent with the sloping, <111>-oriented sidewalls of the anisotropically wet-etched silicon master (~55 degrees) used to shape the PDMS mold.

Microneedle Fabrication Process does not Disrupt the Biotin Binding Activity of Streptavidin (SA).

To test whether the binding activity of a protein is preserved after the process of forming a PVP-protein microneedle, we prepared microneedles that contain streptavidin (SA). SA is tetrameric (MW ~66 kDa) and binds four biotins with high affinity ($K_D$ approximately $10^{-14}$ M). The binding sites for biotin lie at the interfaces of the subunits of SA, so if formation of the microneedles disrupted the quaternary or tertiary structure of SA, we would expect poor binding of biotin. We prepared PVP microneedles with SA and evaluated the biotin binding activity of SA recovered from the microneedles.

The SA microneedles were prepared using the same method with a 100/1 ratio (w/w) of PVP to SA. The SA microneedles were dissolved in $H_2O$ and mixed with biotin-HRP. The level of unbound biotin was then measured with a biotin quantitation kit. The level of decrease in free biotin indicates the level of biotin binding activity of SA in the microneedles. To evaluate the function of recovered SA, we compared the re-dissolved PVP-SA microneedles with microneedles prepared by photochemical crosslinking (Sullivan et al. (2010) Nature Medicine 16:915-20). As a reference, we used an un-polymerized mixture of SA and PVP (mixed in the same weight ratios). We found a similar amount of decrease of free biotin among the samples, corresponding to 90.8% and 81.6% of SA still active in the microneedles respectively (FIG. 4A). This result indicates that protein function and conformation are preserved after the fabrication of microneedles.

To further analyze the SA after formation into PVP-SA microneedles, we dissolved microneedles prepared as above and analyzed using SDS-PAGE (FIG. 4B). We found, as expected, that monomeric SA ran at about ~16 kDa (Lane 1). In the SA obtained from dissolving PVP-SA microneedles, we found bands at ~16 kDa and 66 kDa, corresponding to monomeric and tetrameric (intact) SA (Lane 2). We also saw a high molecular weight, probably multimeric complex. In dissolving PVP-SA microneedles that were fabricated by the photocrosslinking process, we saw no bands, as the very high molecular weight PVP-SA created by photo-crosslinking could not enter into the gel (Lane 3). These results show that in our formulation of PVP microneedles, streptavidin can form a non-covalent complex with PVP and can retain quaternary structure and binding activity. Taken together, these results show that the method of fabrication presented here results in intact, active proteins.

In Vitro Human Foreskin Test.

Figure 5B:
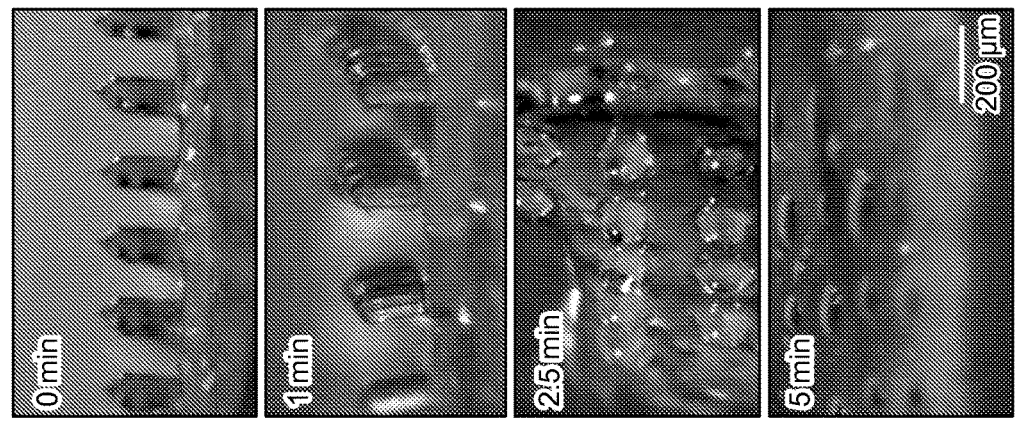
FIG. 5A-5B. Penetration of casein microneedles into human foreskin.
Figure 5A:
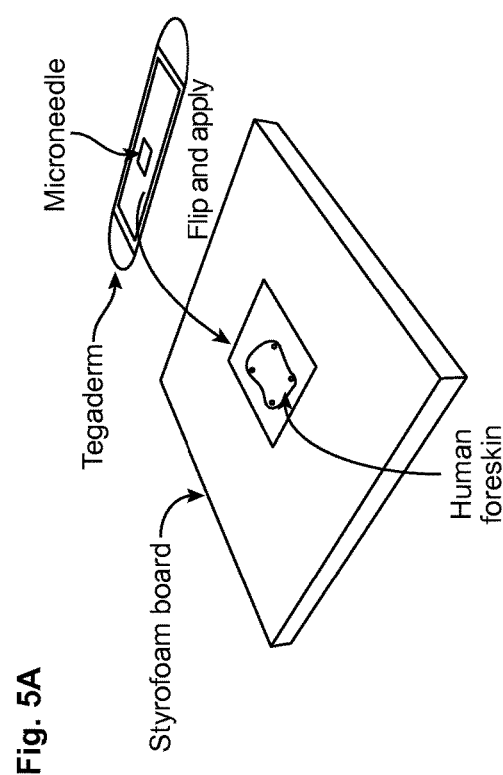

To test the capability of these microneedles to penetrate into human skin, we applied the fluorescently labeled allergen microneedles onto human foreskin. Since human foreskin is soft and pliant, we first pinned it to a Styrofoam board (FIG. 5A). To characterize the kinetics of microneedle dissolution in the foreskin, we inserted microneedles into foreskin and monitored them over time by removing the needles at a set time, then imaged by wide field microscopy. Significant dissolution was observed after 2.5 min, and after 5 min the microneedles were completely dissolved (FIG. 5B). To evaluate the delivery of proteins into the skin, we imaged the skin by fluorescence microscopy after application of microneedles comprising rhodamine B-labeled casein. Fluorescence from the rhodamine was observed up to 187 μm beneath the epidermis. Taken together, these results show that the PVP microneedles can rapidly dissolve and successfully deliver proteins into the dermal portions of the skin.

Comparison of Penetration of Steel Needles and Polymer Microneedles.

Because metal needles are so commonly used for delivering antigens in the skin (e.g., skin prick testing), we compared the capability of our PVP microneedles to deliver antigenic proteins with metal needles. We coated Adminpatch array 1200 steel needles with rhodamine B-labeled casein, and compared with our PVP microneedles containing the same labeled casein protein. The steel needles showed clear penetration, and upon removal, tearing of the skin tissue (FIG. 6). Fluorescence imaging showed that most of the casein was pushed off the needle just at the surface of the skin, with poor delivery below the superficial epidermis. On the other hand, the polymer microneedles showed good penetration, and casein fluorescence was seen spread widely to about 100 μm deep. The results show that the PVP microneedles result in less apparent tissue trauma and deliver antigen more deeply than conventional steel microneedles.

Preparation of Microneedle Arrays.

Figure 7A:
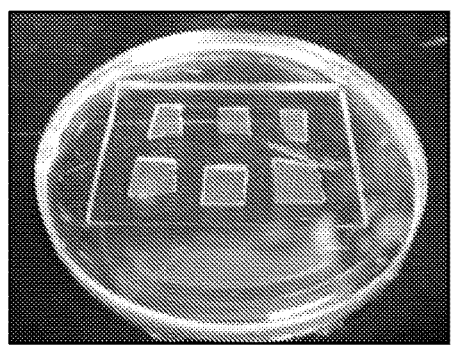
FIG. 7A-7D. Array of microneedles.
Figure 7B:
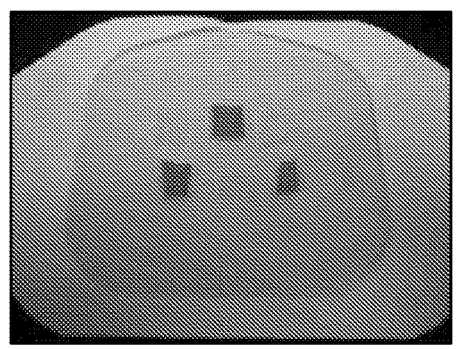
Figure 7C:
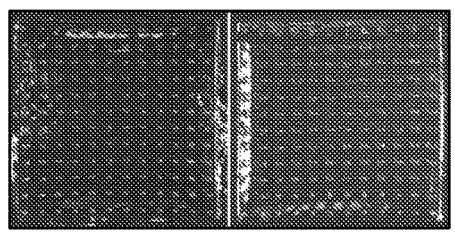
Figure 7D:
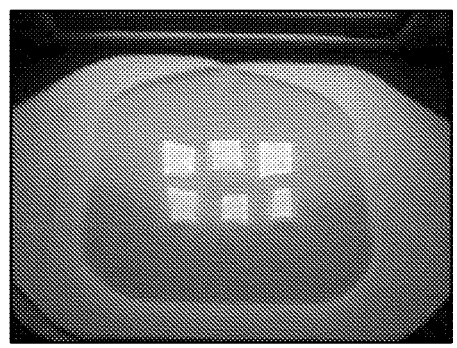
Figure 8:
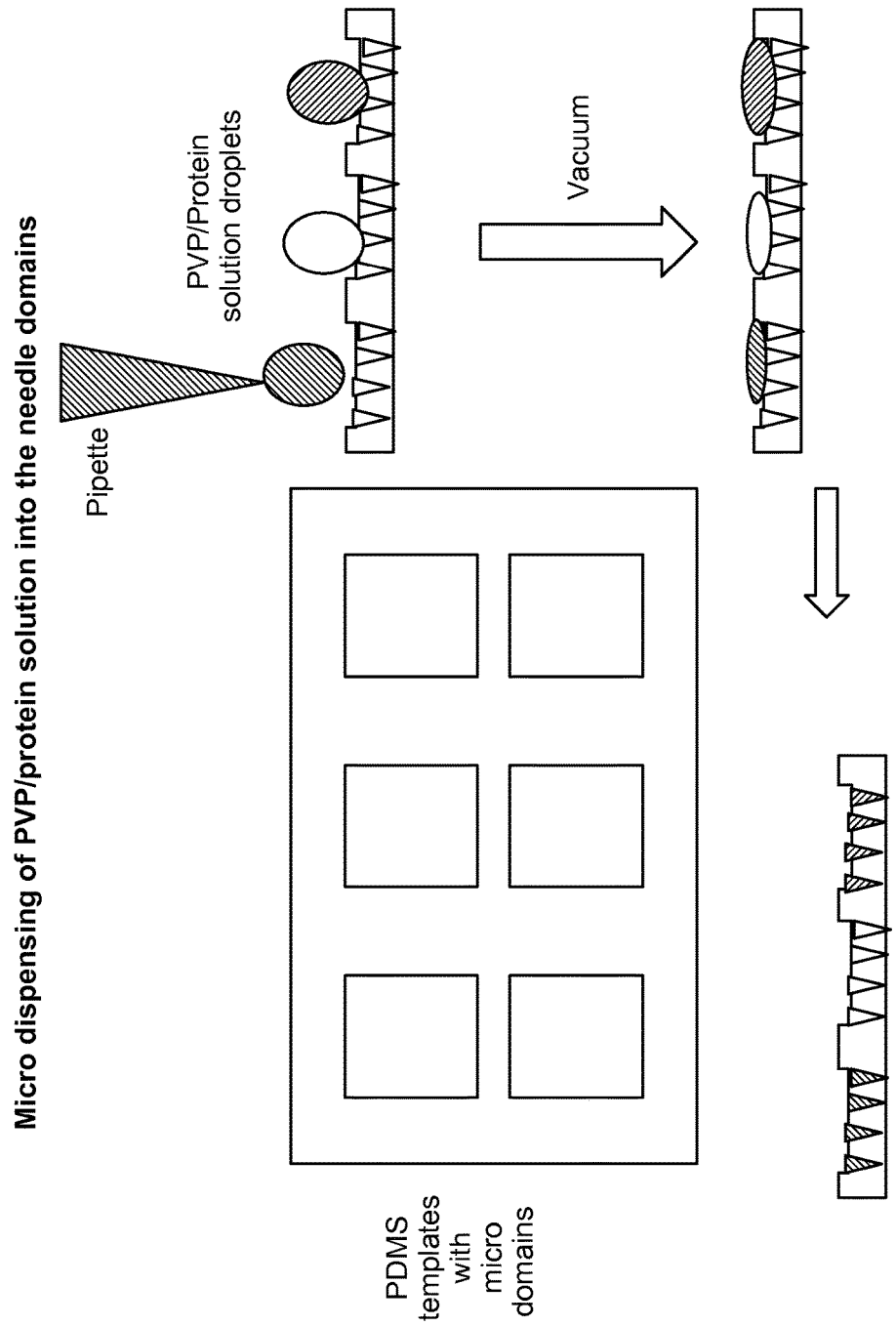
FIG. 8. A schematic representation of the microneedle casting process.

In the clinical setting, skin prick testing often requires multiple allergens to be evaluated in one encounter. We therefore tested the capacity of the PVP microneedles platform to incorporate multiple allergens. A six-patch microneedle array was developed as a proof-of-concept model. A PDMS mold was first prepared that has six wells for six separate microneedle patches (FIG. 7A). PVP microneedles labeled with fluorescein or rhodamine B were cast into the mold in a checkerboard pattern and mounted onto a single Tegaderm patch (FIG. 7B). The needles in each patch were well formed (FIG. 7C). Fluorescence from each domain of the multi-patch array was detected after excitation with a UV lamp (FIG. 7D).

Polymeric microneedles made from various biodegradable or dissolving materials have been reported recently, including carboxymethylcellulose (CMC) (Lee et al. (2011) Small 7:531-9), maltose (Lee et al. (2011) Biomaterials 32:3134-40), poly(lactic-co-glycolic acid) (PLGA) (Park et al. (2006) Pharm Res. 2006; 23:1008-19), and chitosan (Chen et al. (2012) Biomacromolecules 13:4022-31), in addition to PVP. Compared to these formulations, the microneedles of the present invention offer multiple advantages.

First, the conditions used during manufacturing are mild and the process is simple, inexpensive, and easily scaled. Allergen proteins are dissolved in aqueous solution and the micromolding is completed in one step at room temperature, and the process works with peptides, full proteins, and non-protein components. In contrast, high temperature is used to melt PLGA polymers and maltose, which may damage peptides and proteins. As shown in FIG. 4B, PVP microneedles prepared by photo-polymerization caused extensive cross-linking of encapsulated proteins. A recent report described a separable arrowhead PVP microneedle prepared without using photopolymerization (Chu and Prausnitz (2011) J Control Release 149:242-9). However, in this method, polymer microneedle tips need to be mounted on a steel shaft to enhance penetration which increases the complexity and cost of the fabrication process.

Second, with the compositions of the present methods, the needle dissolution is rapid which is especially favorable in clinical practice. As shown in the human foreskin test (FIG. 5), complete dissolution was observed after 5 min. This is in contrast to published CMC microneedles, which showed incomplete dissolution after 24 h insertion in rat skin. The addition of trehalose increased the water solubility. But complete needle dissolution still required several hours. PLGA and chitosan microneedles showed even slower release of encapsulated proteins, lasting for days. In another report, human growth hormone (hGH) was encapsulated in CMC to prepare microneedles using a simple and mild fabrication method which did not affect the functional activity of the hGH. However, the kinetics of dissolution of these microneedles were not suitable for use in allergen skin testing. These other microneedles may be useful in continuous delivery of therapeutics over a long period of time, but not suitable for conducting an allergy skin test, which requires fast delivery.

Although dissolvable polymeric microneedles have gained considerable attention in recent years as a superior method for transdermal drug and vaccine delivery, few reports has explored their utility in allergy skin test. As discussed in US Patent Application 20100030100A1, microneedles have been proposed for the diagnosis of allergy, but in this patent, protein were loading by surface coating, which is cumbersome and inefficient, and furthermore, PVP could not be used successfully.

In summary, we present a technique of fabricating microneedles with PVP that offers the capability of delivering multiple, intact proteins or peptides to the skin for diagnostic or therapeutic applications. When applied to testing linear epitopes of food allergens, this approach offers advantages for easy, low-cost, and functional testing of thousands of epitopes in parallel.

What is claimed is:

1. A method comprising:
   contacting the skin of an individual with a dissolving microneedle array comprising a spatial array of a plurality of epitopes corresponding to one or more proteins suspected of being an allergen for the individual, wherein microneedles in the array are formed of a dissolving polymeric material and encapsulate within the polymeric material at least one epitope for an allergen of interest;
   pressing the microneedle array into the skin to deliver the epitopes to the intradermal skin; and following dissolution of the microneedles capturing one or more images at the site where the microneedle array has penetrated the skin.

2. A method comprising:

contacting the skin of an individual with a dissolving microneedle array comprising a spatial array of a plurality of epitopes corresponding to one or more proteins suspected of being an allergen for the individual, wherein microneedles in the array are formed of dissolving polyvinylpyrrolidone cast in a mold in the substantial absence of photocrosslinking agents and encapsulate within the dissolving polyvinylpyrrolidone at least one epitope for an allergen of interest wherein the microneedle array comprises at least 100 epitopes pressing the microneedle array into the skin to deliver the epitopes to the intradermal skin; and following dissolution of the microneedles capturing one or more images at the site where the microneedle array has penetrated the skin.

3. The method of claim 2, wherein the microneedle array comprises at least 1000 epitopes.

4. The method of claim 2, wherein epitopes from a plurality of proteins are provided in the microneedle array.

5. The method of claim 2, wherein the microneedle array as adhered to a backing.

6. The method of claim 5, wherein the backing comprises an adhesive to adhere to the skin of the individual.

7. The method of claim 5, wherein the backing is a rigid material transparent to infrared radiation.

8. The method of claim 2, wherein the images are visual images.

9. The method of claim 2, wherein the images are thermal images.

10. The method of claim 8, wherein the images are captured at one or more time points between 10 seconds and 15 minutes.

11. The method of claim 2, wherein an imaging device is adhered to the microneedle array.

12. The method of claim 2, wherein an imaging device is adhered to the skin of the individual.

13. A method comprising:

producing a dissolving microneedle array formed of a dissolving polymeric material comprising a spatial array of a plurality of epitopes within the polymeric material, the epitopes corresponding to one or more proteins suspected of being an allergen for an individual, wherein the microneedles are formed in a mold that comprises a planar surface patterned to provide for a superhydrophobic surface;

contacting the skin of the individual with the dissolving microneedle array;

pressing the microneedle array into the skin to deliver the epitopes to the intradermal skin;

following dissolution of the microneedles capturing one or more images at the site where the microneedle array has penetrated the skin.

14. The method of claim 4, wherein the peptides are linear epitopes from one or a plurality of proteins of interest.

15. The method of claim 14, wherein the peptides provide conformational epitopes from one or a plurality of proteins of interest.

16. The method of claim 2, wherein a biological macromolecule corresponding to an epitope is encapsulated within a microneedle in the array at a dose per microneedle of from 1 ng/microneedle to 10 µg/microneedle.

17. The method of claim 2, wherein the microneedles are from 250 to 750 µm in length.

18. The method of claim 2, wherein the array comprises at least $10^2$ microneedles.

19. The method of claim 2, wherein polyvinylpyrrolidine (PVP) is present in the polymer array mixture in an aqueous or ethanolic solution at a concentration of from 25 to 250 mg/ml; polyethylene glycol (PEG) is present at a concentration of from 1:1000 v/v to 25:1000 v/v, the biological macromolecule is present at from 0.01% w/w of PVP to 5% w/w PVP; and the polymer array mixture is substantially free of photocrosslinking agents.

20. A system for use in performing the method of claim 1, comprising:

dissolving microneedle array comprising a spatial array of a plurality of epitopes corresponding to one or more proteins suspected of being an allergen, wherein selected microneedles in the array contain at least one epitope for an allergen of interest; and an imaging device.

21. The system of claim 20, wherein the imaging device is a thermal camera.

* * * * *